United States Patent
Wong, Jr. et al.

(10) Patent No.: US 10,370,662 B2
(45) Date of Patent: *Aug. 6, 2019

(54) REPLICATION CAPABLE RAAV VECTORS ENCODING INHIBITORY SIRNA AND METHODS OF THEIR USE

(71) Applicant: CITY OF HOPE, Duarte, CA (US)

(72) Inventors: Kamehameha K. Wong, Jr., Altadena, CA (US); Cam Mroske, Monrovia, CA (US); Saswati Chatterjee, Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,447

(22) Filed: Oct. 9, 2017

(65) Prior Publication Data
US 2018/0030449 A1 Feb. 1, 2018

Related U.S. Application Data

(63) Continuation of application No. 14/194,538, filed on Feb. 28, 2014, now Pat. No. 9,783,805.

(60) Provisional application No. 61/770,982, filed on Feb. 28, 2013.

(51) Int. Cl.
*C12N 15/113* (2010.01)

(52) U.S. Cl.
CPC ...... *C12N 15/1131* (2013.01); *C12N 2330/51* (2013.01)

(58) Field of Classification Search
CPC ...... A61K 31/513; A61K 48/00; C12N 15/86; C12N 15/113; C12N 2760/16032
USPC ......... 424/93.2; 435/6.1, 91.1, 91.31, 235.1; 536/23.1, 24.5, 23.72
See application file for complete search history.

(56) References Cited

U.S. PATENT DOCUMENTS

| | | | | |
|---|---|---|---|---|
| 9,783,805 B2 * | 10/2017 | Wong, Jr. | ........... | C12N 15/1131 |
| 2008/0108582 A1 | 5/2008 | Kazhdan | | |
| 2010/0297084 A1* | 11/2010 | Bennett | ........... | C12N 15/86 424/93.2 |
| 2012/0087973 A1* | 4/2012 | Lieberman | ........ | C12N 15/1131 424/450 |
| 2014/0322184 A1 | 10/2014 | Farfournoux et al. | | |
| 2015/0044667 A1* | 2/2015 | Crino | ........... | G01N 33/56983 435/5 |
| 2015/0265586 A1* | 9/2015 | Zhang | ........... | C07D 471/04 514/300 |
| 2016/0024173 A1* | 1/2016 | Paterson | ........... | A61K 39/0011 424/190.1 |
| 2016/0053232 A1* | 2/2016 | Gruber | ........... | A61K 38/2292 424/93.2 |

OTHER PUBLICATIONS

Amarzguioui, M., et al., "An Algorithm for Selection of Functional siRNA Sequences," Biochem. Biophys. Res. Commun. 316:1050-1058 (2004).
Amarzguioui, M., et al., "Rational Design and In Vitro and In Vivo Delivery of Dicer Substrate siRNA," Nat. Protocols 1(2):508-517 (2006).
Castanotto, D., et al., "Functional siRNA Expression from Transfected PCR Products," RNA 8:1454-1460 (2002).
Eckstein, A., et al., "Inhibition of Adenovirus Infections by siRNA-Mediated Silencing of Early and Late Adenoviral Gene Functions," Antiviral Res. 88:86-94 (2010).
Hsieh, A. C., et al., "A Library of siRNA Duplexes Targeting the Phosphoinositide 3-Kinase Pathway: Determinants of Gene Silencing for Use in Cell-Based Screens," Nucleic Acids Res. 32(3):893-901 (2004).
Kim, D.H., et al., "Interferon Induction by siRNAs and ssRNAs Synthesized by Phage Polymerase," Nat. Biotechnol. 22(3):321-325 (2004).
Kim, D.H., et al., "Synthetic dsRNA Dicer Substrates Enhance RNAi Potency and Efficacy," Nat. Biotech. 23(2):222-226 (2005).
Lee, N. S., et al., "Expression of Small Interfering RNAs Targeted Against HIV-1 rev Transcripts in Human Cells," Nat. Biotechnol. 20:500-505 (2002).
Reynolds, A., et al., "Rational siRNA Design for RNA Interference," Nat. Biotechnol. 22(3):326-330 (2004).
Saetrom, P., et al., "A Comparison of siRNA Efficacy Predictors," Biochem. Biophys. Res. Commun. 321:247-253 (2004).
Shabalina, S. A., et al., "Computational Models with Thermodynamic and Composition Features Improve siRNA Design," BMC Bioinformatics 7:65 (2006).
Takasaki, S., et al., "An Effective Method for Selecting siRNA Target Sequences in Mammalian Cells," Cell Cycle 3(6):790-795 (2004).
Ui-Tei, K., et al., "Guidelines for the Selection of Highly Effective siRNA Sequences for Mammalian and Chick RNA Interference," Nucleic Acids Res. 32(3):936-948 (2004).

* cited by examiner

*Primary Examiner* — Jane J Zara
(74) *Attorney, Agent, or Firm* — Perkins Coie LLP; Lara J. Dueppen; Yang Tang

(57) ABSTRACT

In some embodiments, an antiviral vector is provided. The antiviral vector includes a replication competent adeno-associated virus (AAV) and an inhibitory expression cassette that includes a nucleotide sequence that encodes an RNAi molecule that inhibits expression of a targeted helper virus (THV) gene. The THV gene may be part of an Adenovirus (Ad) genome, a Human Papillomavirus (HPV) genome, a Human Herpes Virus (HHV) genome, or a Vaccinia virus (VV) genome.

13 Claims, 13 Drawing Sheets

Specification includes a Sequence Listing.

FIG. 2

HPV E6/7 INHIBITORS DESIGNED USING ROSSI ALGORITHM

HPV31-shRNA1

GTGGAAAGGACGAAACACC████████████████████████████████GATATCAAGT (SEQ ID NO:4)

Complement

ACTTGATATCAAAAAACTGCAGAAAGACCTGGAAACTACACAAATTTCCGAGGTCTTTCTGCAGCGGTGTTTCGTCCTTTCCAC (SEQ ID NO:9)

HPV31-shRNA2

GTGGAAAGGACGAAACACC████████████████████████████████GATATCAAGT (SEQ ID NO:5)

Complement

ACTTGATATCAAAAAGGACGACACACCACACGGAGTTCTCTTGAAACTCCGTGTGGTGTGTCGTCCGGTGTTTCGTCCTTTCCAC (SEQ ID NO:10)

HPV31-shRNA3

GTGGAAAGGACGAAACACC████████████████████████████████GATATCAAGT (SEQ ID NO:6)

Complement

ACTTGATATCAAAAAGAGAAGACCTCGTACTGAACTACACAAATTCAGTACGAGGTCTTCTCGGTGTTTCGTCCTTTCCAC (SEQ ID NO:11)

HPV31-shRNA4

GTGGAAAGGACGAAACACC████████████████████████████████GATATCAAGT (SEQ ID NO:7)

Complement

ACTTGATATCAAAAAGTACACGGAGTGTGTACAAACTACACAAATTTGTACACACTCCGTGTGGCGGTGTTTCGTCCTTTCCAC (SEQ ID NO:12)

HPV31-shRNA5

GTGGAAAGGACGAAACACC████████████████████████████████GATATCAAGT (SEQ ID NO:8)

Complement

ACTTGATATCAAAAAGAGCAATTACCCGACAGCTCACTACACAAATGAGCTGTCGGGTAATTGCTCGGTGTTTCGTCCTTTCCAC (SEQ ID NO:13)

FIG. 5

| Target sequence coordinate | Oligo number | Sense strand of the stem | Antisense strand | Duplex stability ( delta G in kcal/mol) | Specificity score | |
|---|---|---|---|---|---|---|
| | | | | | | E6* |
| 239 | 10 | GGTATAGATATAGTGTGTA | TACACACTATATCTATACC | -28.22 | 512.47 | Intron |
| | | | | | | After Intron |
| | | | | | | E7 |
| 795 | 26 | CGGGATGCAATGGTTGGTT | AACCAACCATTGCATCCCG | -34.63 | 623.27 | |
| 796 | 27 | GGGATGCAATGGTTGGTTT | AAACCAACCATTGCATCCC | -33.2 | 900.28 | |
| 847 | 28 | GGACAACATTTCAGAGGAt | GTCCTCTGAAATGTTGTCC | -33.02 | 235.46 | |
| 891 | 29 | GGGAGGATATGGTTGACTT | AAGTCAACCATATCCTCCC | -33.89 | 734.07 | |
| 892 | 30 | GGAGGATATGGTTGACTTT | AAAGTCAACCATATCCTCC | -31.56 | 623.27 | |
| 895 | 31 | GGATATGGTTGACTTTATT | AATAAAGTCAACCATATCC | -27.23 | 567.87 | |
| 901 | 32 | GGTTGACTTTATTGACAAT | ATTGTCAATAAAGTCAACC | -27.05 | 180.06 | |
| 1019 | 33 | CGAAAGTATGTAGGTAGTt | GACTACCTACATACTTTCG | -30.58 | 235.46 | |
| 1031 | 34 | GGTAGTCCTTTAAGTGATA | TATCACTTAAAGGACTACC | -29.49 | 180.06 | |
| 1127 | 35 | CGAAGACTCTTTGAACTTt | GAAGTTCAAAGAGTCTTCG | -29.67 | 69.25 | |
| 1153 | 36 | CGGGTATGGCAATACTGAA | TTCAGTATTGCCATACCCG | -33.07 | 180.06 | |
| 1160 | 37 | GGCAATACTGAAGTGGAAA | TTTCCACTTCAGTATTGCC | -31.31 | 567.87 | |
| 1161 | 38 | GCAATACTGAAGTGGAAAt | GTTTCCACTTCAGTATTGC | -30.74 | 401.66 | |
| 1174 | 39 | GGAAACGCAGCAGATGGTA | TACCATCTGCTGCGTTTCC | -35 | 567.87 | |
| 1195 | 40 | GGTAGAGGAGCAACAAAtA | TGTTTGTTGCTCCTCTACC | -33.6 | 1011.08 | |
| 1201 | 41 | GGAGCAACAAACAACATTA | TAATGTTGTTTGTTGCTCC | -28.67 | 900.28 | |
| 1253 | 42 | CGAGAGAATGAAACTCCAA | TTGGAGTTTCATTCTCTCG | -30.44 | 678.67 | |
| 1302 | 43 | GCAATGGTAAAGCTGCTAT | ATAGCAGCTTTACCATTGC | -31.76 | 69.25 | |
| 1313 | 44 | GCTGCTATGTTAGGTAAAT | ATTTACCTAACATAGCAGC | -29.8 | 180.06 | |
| 1418 | 45 | GCGTTTGGAGTTACAGGTA | TACCTGTAACTCCAAACGC | -32.76 | 401.66 | |
| 1419 | 46 | CGTTTGGAGTTACAGGTAt | GTACCTGTAACTCCAAACG | -32.26 | 180.06 | |
| 1433 | 47 | GGTACAGTTGCAGAAGGAT | ATCCTTCTGCAACTGTACC | -34 | 401.66 | |
| 1465 | 48 | GCAACCATATTGTTTGTAT | ATACAAACAATATGGTTGC | -27.3 | 124.65 | |
| 1469 | 49 | CCATATTGTTTGTATTGtt | GGCAATACAAACAATATGG | -28.54 | 512.47 | |
| 1515 | 50 | GCATGGTTATGTTAATGtT | AGCATTAACATAACCATGC | -29.4 | 346.26 | |
| 1625 | 51 | CCACCCAAATTACGTAGtA | TGCTACGTAATTTGGGTGG | -32.79 | 567.87 | |
| 1641 | 52 | GCACAGCTGCAGCATTATA | TATAATGCTGCAGCTGTGC | -33.82 | 69.25 | |
| 1649 | 53 | GCAGCATTATATTGGTAtA | TGTACCAATATAATGCTGC | -29.8 | 13.85 | |
| 1652 | 54 | GCATTATATTGGTACAGAA | TTCTGTACCAATATAATGC | -27.55 | 69.25 | |
| 1662 | 55 | GGTACAGAACAGGAATGTt | GACATTCCTGTTCTGTACC | -33.31 | 346.26 | |
| 1689 | 56 | GCGATGTATATGGTGAAAt | GTTTCACCATATACATCGC | -30.61 | 235.46 | |
| 1690 | 57 | CGATGTATATGGTGAAAtA | TGTTTCACCATATACATCG | -28.85 | 180.06 | |
| 1709 | 58 | CCAGAATGGATAGAAAGAt | GTCTTTCTATCCATTCTGG | -30.94 | 734.07 | |
| 1774 | 59 | CCAAATGGTACAATGGGtA | TGCCCATTGTACCATTTGG | -33.36 | 235.46 | |

FIG. 5 (continued)

| | | | | | | |
|---|---|---|---|---|---|---|
| 1780 | 60 | GGTACAATGGGCATATGAt | GTCATATGCCCATTGTACC | -33.6 | 180.06 | |
| 1789 | 61 | GGCATATGACAATGATGTT | AACATCATTGTCATATGCC | -29.55 | 124.65 | |
| 1790 | 62 | GCATATGACAATGATGTTA | TAACATCATTGTCATATGC | -27.39 | 69.25 | |
| 1810 | 63 | GGATGATAGTGAAATTGtt | GGCAATTTCACTATCATCC | -31.06 | 235.46 | |
| 1826 | 64 | GCCTATAAATATGCACAAT | ATTGTGCATATTTATAGGC | -27.71 | 180.06 | |
| 1916 | 65 | GGAACAATGTGTAGACATT | AATGTCTACACATTGTTCC | -29.31 | 180.06 | |
| 1952 | 66 | CGACAAATGTCCATGGGAt | GTCCCATGGACATTTGTCG | -34.41 | 124.65 | |
| 1962 | 67 | CCATGGGACAGTGGATTAA | TTAATCCACTGTCCCATGG | -33.68 | 180.06 | |
| 2016 | 68 | GGAGGGACATAGTAAAGTT | AACTTTACTATGTCCCTCC | -31.65 | 623.27 | |
| 2129 | 69 | GGTGCACCTAATACAGGTA | TACCTGTATTAGGTGCACC | -33.99 | 69.25 | |
| 2132 | 70 | GCACCTAATACAGGTAAAT | ATTTACCTGTATTAGGTGC | -29.8 | 235.46 | |
| 2135 | 71 | CCTAATACAGGTAAATCAT | ATGATTTACCTGTATTAGG | -27.59 | 180.06 | |
| 2159 | 72 | GGAATGAGCCTTATTAGtT | AGCTAATAAGGCTCATTCC | -31.69 | 69.25 | |
| 2255 | 73 | GGCATGTTAGATGATGCTA | TAGCATCATCTAACATGCC | -31.85 | 235.46 | |
| 2256 | 74 | GCATGTTAGATGATGCTAt | GTAGCATCATCTAACATGC | -31.51 | 69.25 | |
| 2305 | 75 | CCTACGAAATGCACTAGAT | ATCTAGTGCATTTCGTAGG | -31.18 | 180.06 | |
| 2309 | 76 | CGAAATGCACTAGATGGtA | TGCCATCTAGTGCATTTCG | -32.94 | 235.46 | |
| 2329 | 77 | CCCTGTATCTATAGATGTA | TACATCTATAGATACAGGG | -30.1 | 69.25 | |
| 2330 | 78 | CCTGTATCTATAGATGTAA | TTACATCTATAGATACAGG | -28 | 13.65 | |
| 2378 | 79 | CCTCCTTTATTGATTACAT | ATGTAATCAATAAAGGAGG | -27.3 | 567.87 | |
| 2408 | 80 | GCAGGTAAGGATGACAGAT | ATCTGTCATCCTTACCTGC | -34.28 | 567.87 | |
| 2429 | 81 | CCATACCTACATAGCAGAt | GTCTGCTATGTAGGTATGG | -33.77 | 567.87 | |
| 2491 | 82 | CGGAAATCCAGTATATGAA | TTCATATACTGGATTTCCG | -28.77 | 235.46 | |
| 2492 | 83 | GGAAATCCAGTATATGAAT | ATTCATATACTGGATTTCC | -27.74 | 180.06 | |
| 2544 | 84 | GGACCTGGTGCAGATTAAA | TTTAATCTGCACCAGGTCC | -32.9 | 401.06 | E1* |
| 2547 | 85 | CCTGGTGCAGATTAAATTT | AAATTTAATCTGCACCAGG | -28.01 | 180.06 | After Intron |
| 2550 | 86 | GGTGCAGATTAAATTTGtA | TGCAAATTTAATCTGCACC | -28.94 | 124.65 | |
| 2566 | 87 | GCACGAGGAAGAGGACAAA | TTTGTCCTCTTCCTCGTGC | -34.86 | 1343.49 | |
| 2568 | 88 | CGAGGAAGAGGACAAAGAA | TTCTTTGTCCTCTTCCTCG | -32.57 | 1731.3 | |
| 2690 | 89 | CGATGGAGACTCTTTCtA | TGAGAAAGAGTCTCCATCG | -33.01 | 69.25 | |
| 2727 | 90 | GCAAGAGAAATGGGAATAt | GTATTCCCATTTCTCTTGC | -30.85 | 900.28 | E2/E4 |

Everything downstream should target transcripts

| 4020 | 129 | GGTATTGGTATTGGTATAA | TTATACCAATACCAATACC | -27.85 | 623.27 | 3' UTR |

U6 PROMOTER

AAGGTCGGGCAGGAAGAGGGCCTATTTCCCATGATTCCTTCATATTTGCATATACGATATACCATACAGTAGTGTTAGACAGATAATTAGAATTAAT
TTCACTGTAAACACAAAGATATTAGTACAAAATACGTAGAAAGTAATAATTCTTGGCTAGTAGTTTGCAGTTTGCAGTTTAAAATTATGTTTA
AAATGGACTATCATATGCTAACCGTAACTTGAATTTCGATTTCGAAAGTATTTCATTTCGATTTCTTTATATATCTTGTGCGAAAGGACGAAACACC (SEQ ID NO:14)

(482) GTGGAAAGGACGAAACACC*[gtaacga]*GTATTCAAGT (SEQ ID NO:15)
*complement* ACTTGAATACT*[tcgttac]*GGTGTTTCGTCCTTTCCAC (SEQ ID NO:20)

(553) GTGGAAAGGACGAAACACC*[gtaagag]*GTATTCAAGT (SEQ ID NO:16)
*Complement* ACTTGAATACT*[ctcttac]*GGTGTTTCGTCCTTTCCAC (SEQ ID NO:21)

(599) GTGGAAAGGACGAAACACC*[gtaagag]*GTATTCAAGT (SEQ ID NO:17)
*complement* ACTTGAATACT*[ctcttac]*GGTGTTTCGTCCTTTCCAC (SEQ ID NO:22)

(688) GTGGAAAGGACGAAACACC*[gttcgtc]*GTATTCAAGT (SEQ ID NO:18)
*complement* ACTTGAATACT*[gacgaac]*GGTGTTTCGTCCTTTCCAC (SEQ ID NO:23)

(701) GTGGAAAGGACGAAACACC*[gttcgtc]*GTATTCAAGT (SEQ ID NO:19)
*Complement* ACTTGAATACT*[gacgaac]*GGTGTTTCGTCCTTTCCAC (SEQ ID NO:24)

FIG. 7

SEQUENCE LISTING

```
<160> NUMBER OF SEQ ID NOS: 62

<210> SEQ ID NO 1
<211> LENGTH: 780
<212> TYPE: DNA
<213> ORGANISM: Artificial Sequence
<220> FEATURE:
<223> OTHER INFORMATION: HPV31 E6/E& early transcript sense strand

<400> SEQUENCE: 1
taataataat aatcttagta taaaaaagta gggagtgacc gaaagtggtg aaccgaaaac      60
ggttggtata taaagcacat agtattttgt gcaaacctac agacgccatg ttcaaaaatc     120
ctgcagaaag acctcggaaa ttgcatgaac taagctcggc attggaaata ccctacgatg     180
aactaagatt gaattgtgtc tactgcaaag gtcagttaac agaaacagag gtattagatt     240
ttgcatttac agatttaaca atagtatata gggacgacac accacacgga gtgtgtacaa     300
aatgtttaag attttattca aaagtaagtg aatttagatg gtatagatat agtgtgtatg     360
gaacaacatt agaaaaattg acaaacaaag gtatatgtga tttgttaatt aggtgtataa     420
cgtgtcaaag accgttgtgt ccagaagaaa aacaaagaca tttggataaa aagaaacgat     480
tccacaacat aggaggaagg tccacaggac gttgcatagc atgttggaga agacctcgta     540
ctgaaaccca agtgtaaaca tgcgtggaga aacacctacg ttgcaagact atgtgttaga     600
tttgcaacct gaggcaactg acctccactg ttatgagcaa ttacccgaca gctcagatga     660
ggaggatgtc atagacagtc cagctggaca agcagaaccg gacacatcca attacaatat     720
cgttaccttt tgttgtcagt gtaagtctac acttcgtttg tgtgtacaga gcacacaagt     780

<210> SEQ ID NO 2
<211> LENGTH: 780
<212> TYPE: DNA
<213> ORGANISM: Artificial Sequence
<220> FEATURE:
<223> OTHER INFORMATION: HPV31 E6/E7 early transcript antisense strand

<400> SEQUENCE: 2
```

```
attattatta ttagaatcat attttttcat ccctcactgg ctttcaccac ttggcttttg      60
ccaaccatat atttcgtgta tcataaaaca cgtttggatg tctgcggtac aagttttag     120 gacgtctttc tggagccttt aacgtacttg attcgagccg taacctttat gggatgctac    180
ttgattctaa cttaacacag atgacgtttc cagtcaattg tctttgtctc cataatctaa    240
aacgtaaatg tctaaattgt tatcatatat ccctgctgtg tggtgtgcct cacacatgtt    300
ttacaaattc taaataagt tttcattcac ttaaatctac catatctata tcacacatac    360
cttgttgtaa tcttttaac tgtttgtttc catatacact aaacaattaa tccacatatt    420
gcacagtttc tggcaacaca ggtcttcttt ttgtttctgt aaacctattt ttctttgcta    480
aggtgttgta tcctccttcc acctgtcctg caacgtatcg tacaacctct tctggagcat    540
gactttgggt tcacatttgt acgcacctct ttgtggatgc aacgttctga tacacaatct    600
aaacgttgga ctccgttgac tggaggtgac aatactcgtt aatgggctgt cgagtctact    660
cctcctacag tatctgtcag gtcgacctgt tcgtcttggc ctgtgtaggt taatgttata    720
gcaatggaaa acaacagtca cattcagatg tgaagcaaac acacatgtct cgtgtgttca    780
```

<210> SEQ ID NO 3
<211> LENGTH: 152
<212> TYPE: PRT
<213> ORGANISM: Artificial Sequence
<220> FEATURE:
<223> OTHER INFORMATION: HPV31 E6 protein

<400> SEQUENCE: 3

```
Met Phe Lys Asn Pro Ala Glu Arg Arg Pro Arg Lys Leu His Glu Leu
1               5                   10                  15

Ser Ser Ala Leu Glu Ile Pro Tyr Asp Glu Leu Arg Leu Asn Cys Val
            20                  25                  30

Tyr Cys Lys Gly Gln Leu Thr Glu Thr Glu Val Leu Asp Phe Ala Phe
        35                  40                  45

Thr Asp Leu Thr Ile Val Tyr Arg Asp Asp Thr Pro His Gly Val Cys
    50                  55                  60

Thr Lys Cys Leu Arg Phe Tyr Ser Lys Val Ser Glu Phe Arg Trp Tyr
65                  70                  75                  80

Arg Tyr Ser Val Tyr Gly Thr Thr Leu Glu Lys Leu Thr Asn Lys Gly
                85                  90                  95

Gly Ile Cys Asp Leu Leu Ile Arg Cys Ile Thr Cys Gln Arg Pro Leu
            100                 105                 110

Cys Pro Glu Glu Lys Gln Arg His Leu Asp Lys Lys Arg Phe His
        115                 120                 125

Asn Ile Gly Gly Arg Val Thr Gly Arg Cys Ile Ala Ala Cys Trp Arg
    130                 135                 140

Arg Pro Arg Thr Glu Thr Gln Val
145                 150
```

<210> SEQ ID NO 4
<211> LENGTH: 85
<212> TYPE: DNA
<213> ORGANISM: Artificial Sequence
<220> FEATURE:
<223> OTHER INFORMATION: HPV31-shRNA1

<400> SEQUENCE: 4

```
gtggaaagga cgaaacaccg ctgcagaaag acctcggaaa tttgtgtagt ttccgaggtc      60
```

```
tttctgcagt tttttgatat caagt                                              85

<210> SEQ ID NO 5
<211> LENGTH: 85
<212> TYPE: DNA
<213> ORGANISM: Artificial Sequence
<220> FEATURE:
<223> OTHER INFORMATION: HPV31-shRNA2

<400> SEQUENCE: 5
gtggaaagga cgaaacaccg gacgacacac cacacggact tcaagagaa ctccgtgtgg        60 tgtgtcgtcc tttttgatat caagt                                              85

<210> SEQ ID NO 6
<211> LENGTH: 81
<212> TYPE: DNA
<213> ORGANISM: Artificial Sequence
<220> FEATURE:
<223> OTHER INFORMATION: HPV31-shRNA3

<400> SEQUENCE: 6
gtggaaagga cgaaacaccg agaagacctc gtactgaatt tgtgtagttc agtacgaggt        60
cttctctttt tgatatcaag t                                                  81

<210> SEQ ID NO 7
<211> LENGTH: 84
<212> TYPE: DNA
<213> ORGANISM: Artificial Sequence
<220> FEATURE:
<223> OTHER INFORMATION: HPV31-shRNA4

<400> SEQUENCE: 7
gtggaaagga cgaaacaccg ccacacggag tgtgtacaaa tttgtgtagt tgtacacac        60 tccgtgtggt ttttgatatc aagt                                               84

<210> SEQ ID NO 8
<211> LENGTH: 85
<212> TYPE: DNA
<213> ORGANISM: Artificial Sequence
<220> FEATURE:
<223> OTHER INFORMATION: HPV31-shRNA5

<400> SEQUENCE: 8
gtggaaagga cgaaacaccg agcaattacc cgacagctca tttgtgtagt gagctgtcgg        60
gtaattgctc tttttgatat caagt                                              85

<210> SEQ ID NO 9
<211> LENGTH: 85
<212> TYPE: DNA
<213> ORGANISM: Artificial Sequence
<220> FEATURE:
<223> OTHER INFORMATION: HPV31-shRNA1 complement

<400> SEQUENCE: 9
acttgatatc aaaaaactgc agaaagacct cggaaactac acaaatttcc gaggtctttc        60
tgcagcggtg tttcgtcctt tccac                                              85

<210> SEQ ID NO 10
<211> LENGTH: 85
<212> TYPE: DNA
<213> ORGANISM: Artificial Sequence
<220> FEATURE:
<223> OTHER INFORMATION: HPV31-shRNA2 complement
```

```
<400> SEQUENCE: 10
acttgatatc aaaaaggacg acacaccaca cggagttctc ttgaaactcc gtgtggtgtg      60
tcgtccggtg tttcgtcctt tccac                                           85

<210> SEQ ID NO 11
<211> LENGTH: 81
<212> TYPE: DNA
<213> ORGANISM: Artificial Sequence
<220> FEATURE:
<223> OTHER INFORMATION: HPV31-shRNA3 complement

<400> SEQUENCE: 11
acttgatatc aaaagagaa gacctcgtac tgaactacac aaattcagta cgaggtcttc       60
tcggtgtttc gtcctttcca c                                               81

<210> SEQ ID NO 12
<211> LENGTH: 84
<212> TYPE: DNA
<213> ORGANISM: Artificial Sequence
<220> FEATURE:
<223> OTHER INFORMATION: HPV31-shRNA4 complement

<400> SEQUENCE: 12
acttgatatc aaaaccaca cggagtgtgt acaaactaca caaatttgta cacactccgt      60
gtggcggtgt ttcgtccttt ccac                                            84

<210> SEQ ID NO 13
<211> LENGTH: 85
<212> TYPE: DNA
<213> ORGANISM: Artificial Sequence
<220> FEATURE:
<223> OTHER INFORMATION: HPV31-shRNA5 complement

<400> SEQUENCE: 13
acttgatatc aaaagagca attacccgac agctcactac acaaatgagc tgtcgggtaa      60
ttgctcggtg tttcgtcctt tccac                                           85

<210> SEQ ID NO 14
<211> LENGTH: 264
<212> TYPE: DNA
<213> ORGANISM: Artificial Sequence
<220> FEATURE:
<223> OTHER INFORMATION: U6 promoter

<400> SEQUENCE: 14
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aaggacgaaa cacc                                           264

<210> SEQ ID NO 15
<211> LENGTH: 81
<212> TYPE: DNA
<213> ORGANISM: Artificial Sequence
<220> FEATURE:
<223> OTHER INFORMATION: shRNA HPV E7 inhibitor U6sh482

<400> SEQUENCE: 15
```

```
gtggaaagga cgaaacaccg caagactatg tgttagattt caagagaatc taacacatag    60
tcttgctttt tgatatcaag t                                              81
```

<210> SEQ ID NO 16
<211> LENGTH: 81
<212> TYPE: DNA
<213> ORGANISM: Artificial Sequence
<220> FEATURE:
<223> OTHER INFORMATION: shRNA HPV E7 inhibitor U6sh482 complement

<400> SEQUENCE: 16

```
gtggaaagga cgaaacaccg gatgtcatag acagtctatt caagagatgg actgtctatg    60 acatccttt tgatatcaag t                                               81
```

<210> SEQ ID NO 17
<211> LENGTH: 81
<212> TYPE: DNA
<213> ORGANISM: Artificial Sequence
<220> FEATURE:
<223> OTHER INFORMATION: shRNA HPV E7 inhibitor U6sh563

<400> SEQUENCE: 17

```
gtggaaagga cgaaacaccg gacacatcca attacaattt caagagaatt gtaattggat    60
gtgtcctttt tgatatcaag t                                              81
```

<210> SEQ ID NO 18
<211> LENGTH: 82
<212> TYPE: DNA
<213> ORGANISM: Artificial Sequence
<220> FEATURE:
<223> OTHER INFORMATION: shRNA HPV E7 inhibitor U6sh563 complement

<400> SEQUENCE: 18

```
gtggaaagga cgaaacaccg catattgcaa gagctgttct tcctgtcaaa cagctcttgc    60
aatatgcttt ttgatatcaa gt                                             82
```

<210> SEQ ID NO 19
<211> LENGTH: 82
<212> TYPE: DNA
<213> ORGANISM: Artificial Sequence
<220> FEATURE:
<223> OTHER INFORMATION: shRNA HPV E7 inhibitor U6sh599

<400> SEQUENCE: 19

```
gtggaaagga cgaaacaccg ctgttaatgg gctcatttct tcctgtcaaa atgagcccat    60
taacagcttt ttgatatcaa gt                                             82
```

<210> SEQ ID NO 20
<211> LENGTH: 81
<212> TYPE: DNA
<213> ORGANISM: Artificial Sequence
<220> FEATURE:
<223> OTHER INFORMATION: shRNA HPV E7 inhibitor U6sh599 complement

<400> SEQUENCE: 20

```
acttgatatc aaaaagcaag actatgtgtt agattctctt gaaatctaac acatagtctt    60
gcggtgtttc gtcctttcca c                                              81
```

<210> SEQ ID NO 21
<211> LENGTH: 81
<212> TYPE: DNA
<213> ORGANISM: Artificial Sequence

```
<220> FEATURE:
<223> OTHER INFORMATION: shRNA HPV E7 inhibitor U6sh688

<400> SEQUENCE: 21
acttgatatc aaaaaggatg tcatagacag tccatctctt gaatagactg tctatgacat    60
ccggtgtttc gtcctttcca c                                              81

<210> SEQ ID NO 22
<211> LENGTH: 81
<212> TYPE: DNA
<213> ORGANISM: Artificial Sequence
<220> FEATURE:
<223> OTHER INFORMATION: shRNA HPV E7 inhibitor U6sh688 complement

<400> SEQUENCE: 22
acttgatatc aaaaaggaca catccaatta caattctctt gaaattgtaa ttggatgtgt    60
ccggtgtttc gtcctttcca c                                              81

<210> SEQ ID NO 23
<211> LENGTH: 82
<212> TYPE: DNA
<213> ORGANISM: Artificial Sequence
<220> FEATURE:
<223> OTHER INFORMATION: shRNA HPV E7 inhibitor U6sh701

<400> SEQUENCE: 23
acttgatatc aaaaagcata ttgcaagagc tgtttgacag gaagaacagc tcttgcaata    60
tgcggtgttt cgtcctttcc ac                                             82

<210> SEQ ID NO 24
<211> LENGTH: 82
<212> TYPE: DNA
<213> ORGANISM: Artificial Sequence
<220> FEATURE:
<223> OTHER INFORMATION: shRNA HPV E7 inhibitor U6sh701 complement

<400> SEQUENCE: 24
acttgatatc aaaaagctgt taatgggctc attttgacag gaagaaatga gcccattaac    60
agcggtgttt cgtcctttcc ac                                             82

<210> SEQ ID NO 25
<211> LENGTH: 100
<212> TYPE: DNA
<213> ORGANISM: Artificial Sequence
<220> FEATURE:
<223> OTHER INFORMATION: H1 promoter

<400> SEQUENCE: 25
aatatttgca tgtcgctatg tgttctggga aatcaccata aacgtgaaat gtctttggat    60
ttgggaatct tataagttct gtatgagacc actcggatcc                          100

<210> SEQ ID NO 26
<211> LENGTH: 83
<212> TYPE: DNA
<213> ORGANISM: Artificial Sequence
<220> FEATURE:
<223> OTHER INFORMATION: shrna hpv e7 inhibitor h1sh521

<400> SEQUENCE: 26
gtatgagacc actcggatcc cctccactgt tatgagcaat tcaagaagat tgctcataac    60
agtggaggtt tttgatatca agt                                            83
```

<210> SEQ ID NO 27
<211> LENGTH: 82
<212> TYPE: DNA
<213> ORGANISM: Artificial Sequence
<220> FEATURE:
<223> OTHER INFORMATION: shRNA HPV E7 inhibitor H1sh521 complement

<400> SEQUENCE: 27
gtatgagacc actcggatcc cccaactgtt ctactagatt tcaagagagt ctactagaac      60
agttgggttt ttgatatcaa gt                                               82

<210> SEQ ID NO 28
<211> LENGTH: 82
<212> TYPE: DNA
<213> ORGANISM: Artificial Sequence
<220> FEATURE:
<223> OTHER INFORMATION: shRNA HPV E7 inhibitor H1sh732

<400> SEQUENCE: 28
gtatgagacc actcggatcc ccggacacat ccaattatat tcaagagatg taattggatg      60
tgtccggttt ttgatatcaa gt                                               82

<210> SEQ ID NO 29
<211> LENGTH: 82
<212> TYPE: DNA
<213> ORGANISM: Artificial Sequence
<220> FEATURE:
<223> OTHER INFORMATION: shRNA HPV E7 inhibitor H1sh732 complement

<400> SEQUENCE: 29
gtatgagacc actcggatcc cggacacatc caattacaat tcaagagatt gtaattggat      60
gtgtccgttt ttgatatcaa gt                                               82

<210> SEQ ID NO 30
<211> LENGTH: 82
<212> TYPE: DNA
<213> ORGANISM: Artificial Sequence
<220> FEATURE:
<223> OTHER INFORMATION: shRNA HPV E7 inhibitor H1sh597

<400> SEQUENCE: 30
gtatgagacc actcggatcc cgtttgtgtg tacagagtat tcaagagatg ctctgtacac      60
acaaacgttt ttgatatcaa gt                                               82

<210> SEQ ID NO 31
<211> LENGTH: 82
<212> TYPE: DNA
<213> ORGANISM: Artificial Sequence
<220> FEATURE:
<223> OTHER INFORMATION: shRNA HPV E7 inhibitor H1sh597 complement

<400> SEQUENCE: 31
gtatgagacc actcggatcc ccactgttat gagcaattat tcaagagata attgctcata      60
acagtggttt ttgatatcaa gt                                               82

<210> SEQ ID NO 32
<211> LENGTH: 83
<212> TYPE: DNA
<213> ORGANISM: Artificial Sequence
<220> FEATURE:
<223> OTHER INFORMATION: shRNA HPV E7 inhibitor H1sh598

<400> SEQUENCE: 32
gtatgagacc actcggatcc cgttgcaaga ctatgtgttc ttcctgtcaa acacatagtc    60
ttgcaacgtt tttgatatca agt                                             83

<210> SEQ ID NO 33
<211> LENGTH: 83
<212> TYPE: DNA
<213> ORGANISM: Artificial Sequence
<220> FEATURE:
<223> OTHER INFORMATION: shRNA HPV E7 inhibitor H1sh598 complement

<400> SEQUENCE: 33
gtatgagacc actcggatcc ccaactgttc tactagattc ttcctgtcaa gtctagtaga    60
acagttggtt tttgatatca agt                                             83

<210> SEQ ID NO 34
<211> LENGTH: 82
<212> TYPE: DNA
<213> ORGANISM: Artificial Sequence
<220> FEATURE:
<223> OTHER INFORMATION: shRNA HPV E7 inhibitor H1sh654

<400> SEQUENCE: 34
acttgatatc aaaaacctcc actgttatga gcaatctctt gaattgctca taacagtgga    60
ggggatccga gtggtctcat ac                                              82

<210> SEQ ID NO 35
<211> LENGTH: 82
<212> TYPE: DNA
<213> ORGANISM: Artificial Sequence
<220> FEATURE:
<223> OTHER INFORMATION: shRNA HPV E7 inhibitor H1sh654 complement

<400> SEQUENCE: 35
acttgatatc aaaaacccaa ctgttctact agactctctt gaaatctagt agaacagttg    60
ggggatccga gtggtctcat ac                                              82

<210> SEQ ID NO 36
<211> LENGTH: 82
<212> TYPE: DNA
<213> ORGANISM: Artificial Sequence
<220> FEATURE:
<223> OTHER INFORMATION: shRNA HPV E7 inhibitor H1sh524

<400> SEQUENCE: 36
acttgatatc aaaaaccgga cacatccaat tacatctctt gaatataatt ggatgtgtcc    60
ggggatccga gtggtctcat ac                                              82

<210> SEQ ID NO 37
<211> LENGTH: 82
<212> TYPE: DNA
<213> ORGANISM: Artificial Sequence
<220> FEATURE:
<223> OTHER INFORMATION: shRNA HPV E7 inhibitor H1sh524 complement

<400> SEQUENCE: 37
acttgatatc aaaaacggac acatccaatt acaatctctt gaattgtaat tggatgtgtc    60
cgggatccga gtggtctcat ac                                              82

<210> SEQ ID NO 38
<211> LENGTH: 82
<212> TYPE: DNA

```
<213> ORGANISM: Artificial Sequence
<220> FEATURE:
<223> OTHER INFORMATION: shRNA HPV E7 inhibitor H1sh478

<400> SEQUENCE: 38
acttgatatc aaaaacgttt gtgtgtacag agcatctctt gaatactctg tacacacaaa    60
cgggatccga gtggtctcat ac                                              82

<210> SEQ ID NO 39
<211> LENGTH: 82
<212> TYPE: DNA
<213> ORGANISM: Artificial Sequence
<220> FEATURE:
<223> OTHER INFORMATION: shRNA HPV E7 inhibitor H1sh478 complement

<400> SEQUENCE: 39
acttgatatc aaaaccact gttatgagca attatctctt gaataattgc tcataacagt      60
ggggatccga gtggtctcat ac                                              82

<210> SEQ ID NO 40
<211> LENGTH: 83
<212> TYPE: DNA
<213> ORGANISM: Artificial Sequence
<220> FEATURE:
<223> OTHER INFORMATION: shRNA HPV E7 inhibitor H1sh733

<400> SEQUENCE: 40
acttgatatc aaaaacgttg caagactatg tgtttgacag gaagaacaca tagtcttgca     60
acgggatccg agtggtctca tac                                             83

<210> SEQ ID NO 41
<211> LENGTH: 83
<212> TYPE: DNA
<213> ORGANISM: Artificial Sequence
<220> FEATURE:
<223> OTHER INFORMATION: shRNA HPV E7 inhibitor H1sh733 complement

<400> SEQUENCE: 41
acttgatatc aaaaccaac tgttctacta gacttgacag gaagaatcta gtagaacagt      60 tgggatccg agtggtctca tac                                              83

<210> SEQ ID NO 42
<211> LENGTH: 20
<212> TYPE: DNA
<213> ORGANISM: Artificial Sequence
<220> FEATURE:
<223> OTHER INFORMATION: HPC31b E6/7 sh1 inhibitor target sequence

<400> SEQUENCE: 42
ctgcagaaag acctcggaaa                                                 20

<210> SEQ ID NO 43
<211> LENGTH: 21
<212> TYPE: DNA
<213> ORGANISM: Artificial Sequence
<220> FEATURE:
<223> OTHER INFORMATION: HPC31b E6/7 sh2 inhibitor target sequence

<400> SEQUENCE: 43
ggacgacaca ccacacggag t                                               21

<210> SEQ ID NO 44
<211> LENGTH: 19
```

```
<212> TYPE: DNA
<213> ORGANISM: Artificial Sequence
<220> FEATURE:
<223> OTHER INFORMATION: HPC31b E6/7 sh3 inhibitor target sequence

<400> SEQUENCE: 44
gagaagacct cgtactgaa                                                19

<210> SEQ ID NO 45
<211> LENGTH: 20
<212> TYPE: DNA
<213> ORGANISM: Artificial Sequence
<220> FEATURE:
<223> OTHER INFORMATION: HPC31b E6/7 sh4 inhibitor target sequence

<400> SEQUENCE: 45
ccacacggag tgtgtacaaa                                               20

<210> SEQ ID NO 46
<211> LENGTH: 21
<212> TYPE: DNA
<213> ORGANISM: Artificial Sequence
<220> FEATURE:
<223> OTHER INFORMATION: HPC31b E6/7 sh5 inhibitor target sequence

<400> SEQUENCE: 46
gagcaattac ccgacagctc a                                             21

<210> SEQ ID NO 47
<211> LENGTH: 19
<212> TYPE: DNA
<213> ORGANISM: Artificial Sequence
<220> FEATURE:
<223> OTHER INFORMATION: HPC31b E7 ORF shE7(521) inhibitor target
      sequence

<400> SEQUENCE: 47
cctccactgt tatgagcaa                                                19

<210> SEQ ID NO 48
<211> LENGTH: 19
<212> TYPE: DNA
<213> ORGANISM: Artificial Sequence
<220> FEATURE:
<223> OTHER INFORMATION: HPC31b E7 ORF shE7(563) inhibitor target
      sequence

<400> SEQUENCE: 48
ggatgtcata gacagtcca                                                19

<210> SEQ ID NO 49
<211> LENGTH: 19
<212> TYPE: DNA
<213> ORGANISM: Artificial Sequence
<220> FEATURE:
<223> OTHER INFORMATION: HPC31b E7 ORF shE7(597) inhibitor target
      sequence

<400> SEQUENCE: 49
ccggacacat ccaattaca                                                19

<210> SEQ ID NO 50
<211> LENGTH: 19
<212> TYPE: DNA
<213> ORGANISM: Artificial Sequence
<220> FEATURE:
<223> OTHER INFORMATION: HPC31b E7 ORF shE7(598) inhibitor target
```

-continued

<210> SEQ ID NO 51
<211> LENGTH: 19
<212> TYPE: DNA
<213> ORGANISM: Artificial Sequence
<220> FEATURE:
<223> OTHER INFORMATION: HPC31b E7 ORF shE7(599) inhibitor target sequence

<400> SEQUENCE: 51
ggacacatcc aattacaat                                              19

<210> SEQ ID NO 52
<211> LENGTH: 19
<212> TYPE: DNA
<213> ORGANISM: Artificial Sequence
<220> FEATURE:
<223> OTHER INFORMATION: HPC31b E7 ORF shE7(688) inhibitor target sequence

<400> SEQUENCE: 52
gcatattgca agagctgtt                                              19

<210> SEQ ID NO 53
<211> LENGTH: 19
<212> TYPE: DNA
<213> ORGANISM: Artificial Sequence
<220> FEATURE:
<223> OTHER INFORMATION: HPC31b E7 ORF shE7(701) inhibitor target sequence

<400> SEQUENCE: 53
gctgttaatg ggctcattt                                              19

<210> SEQ ID NO 54
<211> LENGTH: 19
<212> TYPE: DNA
<213> ORGANISM: Artificial Sequence
<220> FEATURE:
<223> OTHER INFORMATION: AD5 E1A siE1A-4 target sequence (sense)

<400> SEQUENCE: 54
cggaggtgtt attaccgaa                                              19

<210> SEQ ID NO 55
<211> LENGTH: 19
<212> TYPE: DNA
<213> ORGANISM: Artificial Sequence
<220> FEATURE:
<223> OTHER INFORMATION: AD5 IVa2 siIVa2-2 target sequence (sense)

<400> SEQUENCE: 55
gttagtgatc ccagaaata                                              19

<210> SEQ ID NO 56
<211> LENGTH: 19
<212> TYPE: DNA
<213> ORGANISM: Artificial Sequence
<220> FEATURE:
<223> OTHER INFORMATION: AD5 Hexon siHexon-4 target sequence (sense)

<400> SEQUENCE: 56

```
gctagaaagt caagtggaa                                                      19

<210> SEQ ID NO 57
<211> LENGTH: 37
<212> TYPE: DNA
<213> ORGANISM: Artificial Sequence
<220> FEATURE:
<223> OTHER INFORMATION: AD5 shE1A-4 inhibitor

<400> SEQUENCE: 57
cggaggtgtt attaccgaau ucgguaauaa caccucc                                  37

<210> SEQ ID NO 58
<211> LENGTH: 38
<212> TYPE: DNA
<213> ORGANISM: Artificial Sequence
<220> FEATURE:
<223> OTHER INFORMATION: AD5 shIVa2-2 inhibitor

<400> SEQUENCE: 58
gttagtgatc ccagaaatau auuucuggga ucacuaac                                 38

<210> SEQ ID NO 59
<211> LENGTH: 38
<212> TYPE: DNA
<213> ORGANISM: Artificial Sequence
<220> FEATURE:
<223> OTHER INFORMATION: AD5 shHexon-4

<400> SEQUENCE: 59
gctagaaagt caagtggaau uccacuugac uuucuagc                                 38

<210> SEQ ID NO 60
<211> LENGTH: 19
<212> TYPE: DNA
<213> ORGANISM: Artificial Sequence
<220> FEATURE:
<223> OTHER INFORMATION: AD TriP(45) inhibitor target sequence (sense)

<400> SEQUENCE: 60
cggaggtgtt attaccgaa                                                      19

<210> SEQ ID NO 61
<211> LENGTH: 19
<212> TYPE: DNA
<213> ORGANISM: Artificial Sequence
<220> FEATURE:
<223> OTHER INFORMATION: AD TriP(46) inhibitor target sequence (sense)

<400> SEQUENCE: 61
gttagtgatc ccagaaata                                                      19

<210> SEQ ID NO 62
<211> LENGTH: 19
<212> TYPE: DNA
<213> ORGANISM: Artificial Sequence
<220> FEATURE:
<223> OTHER INFORMATION: AD TriP(170) inhibitor target sequence (sense)

<400> SEQUENCE: 62
gctagaaagt caagtggaa                                                      19
```

REPLICATION CAPABLE RAAV VECTORS ENCODING INHIBITORY SIRNA AND METHODS OF THEIR USE

PRIORITY CLAIM

This application is a continuation of U.S. application Ser. No. 14/194,538, filed Feb. 28, 2014, which claims priority to U.S. Provisional Application No. 61/770,982, filed Feb. 28, 2013, which is hereby incorporated herein by reference as if fully set forth herein, including the drawings.

BACKGROUND

Adeno-associated virus (AAV) is a 5 kb nonpathogenic, helper dependent member of the Parvovirus Family. The adeno-associated virus (AAV) genome is built of single-stranded deoxyribonucleic acid (ssDNA), either positive- or negative-sensed, and comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which interact together to form a capsid of an icosahedral symmetry.

Typically, AAV has been utilized as a viral vector by removing endogenous AAV genes, substituting a gene of interest, encapsidating with Ad or herpes simplex (HSV), and purifying the vector away from the helper virus. However, without its endogenous genes, there is limited potential for producing a sufficient amount of the AAV vectors for therapeutic uses. For this and other reasons, it would be beneficial to design an AAV vector that includes endogenous AAV genes.

SUMMARY

In some embodiments, an antiviral vector is provided. The antiviral vector includes a replication competent adeno-associated virus (AAV) and an inhibitory expression cassette that includes a nucleotide sequence that encodes an RNAi molecule that inhibits expression of a targeted helper virus (THV) gene.

In other embodiments, a method of killing a cell infected with a THV is provided. Such a method may include a step of administering an effective amount of an antiviral vector to the cell, wherein the antiviral vector comprises a replication competent AAV virus inserted with a nucleotide sequence that encodes an RNAi molecule that inhibits expression of a targeted helper virus (THV) gene.

In other embodiments, a method of treating or preventing a THV infection in a subject is provided. Such a method may include a step of administering a therapeutically effective dose of a pharmaceutical composition, wherein the pharmaceutical composition comprises a replication competent AAV virus inserted with a nucleotide sequence that encodes an RNAi molecule that inhibits expression of a targeted helper virus (THV) gene.

In other embodiments, a method of producing an antiviral vector is provided. Such a method may include steps of culturing the antiviral vector with a population of cells infected with a first THV, such that the antiviral vector co-infects the population of cells; and isolating the antiviral vector after at least one full infectious cycle; wherein the antiviral vector comprises a replication competent AAV virus and a nucleotide sequence that encodes an RNAi molecule that inhibits expression of a targeted helper virus (THV) gene.

In the embodiments described above, the THV gene may be part of an Adenovirus (Ad) genome, a Human Papillomavirus (HPV) genome, a Human Herpes Virus (HHV) genome, or a Vaccinia virus (VV) genome.

BRIEF DESCRIPTION OF THE DRAWINGS

FIG. 2 shows the sequences of the shRNA HPV E6/7 inhibitors (and complement sequences) designed using the Rossi Algorithm (SEQ ID NOs:4-13).

FIG. 3A shows the efficacy of sh1, sh3, sh4, and sh5. FIG. 3B shows the efficacy of sh2 (which targets the E6 intron and shows the highest inhibition).

FIG. 5 is a table showing the sense and antisense target strands of the HPV31 E6, E7, E1, E2/E4, E5a and the 3' UTR gene regions as identified by the Shabalina Algorithm. 129 targets were identified using −35 to −27 kcal/mol AS-target stability (less stringent), while 84 targets were identified using −33 to −28 kcal/mol (more stringent, recommended for shRNA).

FIG. 6 shows the sequences of the U6 promoter (SEQ ID NO:14) and the shRNA HPV E7 inhibitors (and complement sequences) designed using the Shabalina Algorithm. (SEQ ID NOs:15-24). Arrows indicate inhibitors that showed the greatest activity against specific target gene.

FIG. 7 shows the E7 target sites on HPV31 transcript, selected using the Shabalina Algorithm. The transcript includes the sense and antisense of the E6/7 early transcript. The amino acid sequence of the E7 protein is also shown.

FIG. 12A shows the results of the first trial, which used 60 mm culture dishes, 48 hours after transfection of the targeted inhibitors as indicated. FIG. 12B shows the results of the second trial, which used 6-well dishes, 48 hours after transfection of the targeted inhibitors as indicated.

DETAILED DESCRIPTION

Figure 1:
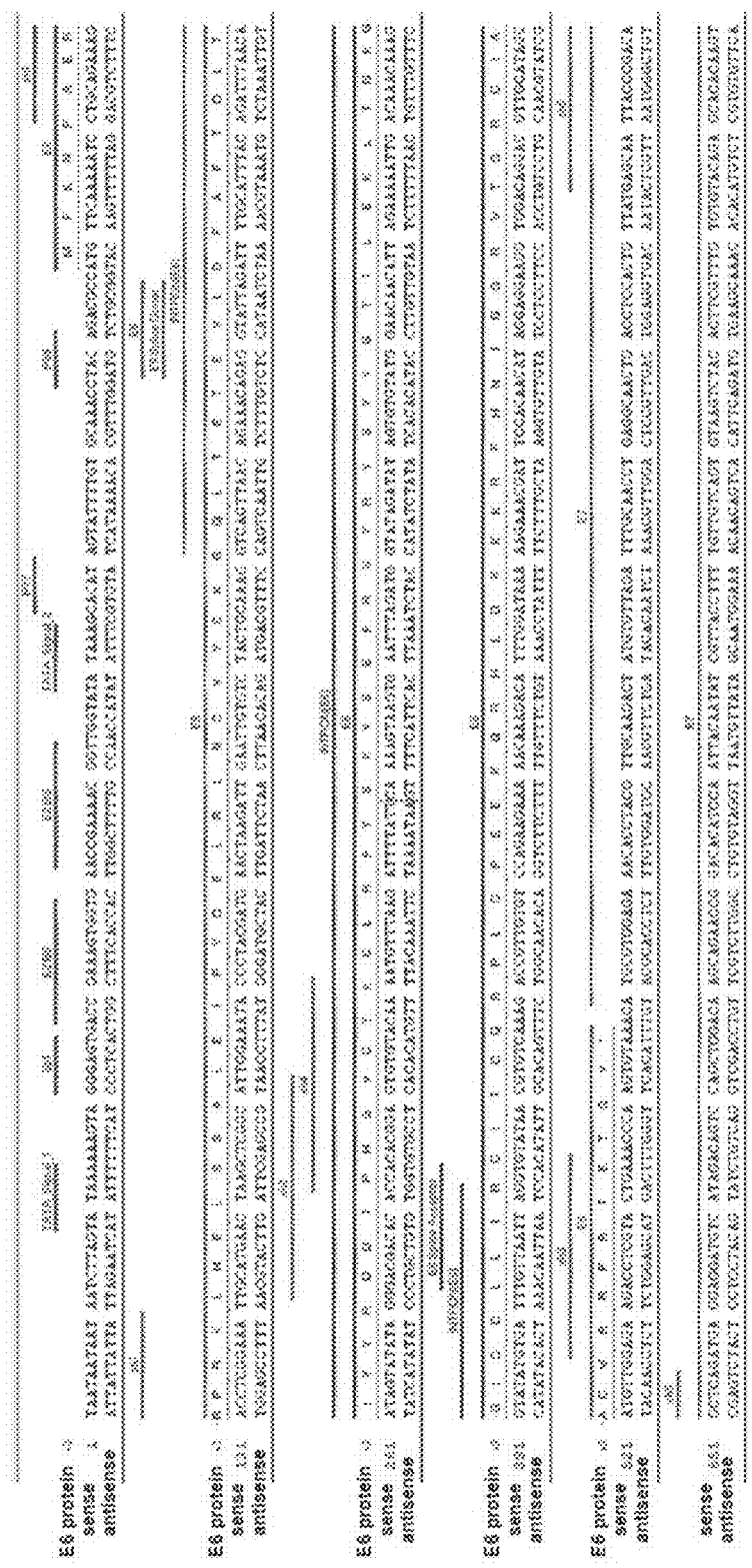
FIG. 1 shows the E6/7 target sites on HPV31b early transcript selected using the Rossi Algorithm. The transcript includes the sense (SEQ ID NO:1) and antisense (SEQ ID NO:2) of the E6/7 early transcript. The amino acid sequence of the E6 protein is also shown (SEQ ID NO:3).

Antiviral vectors that express one or more RNAi molecules that inhibit the expression of one or more targeted helper virus (THV) genes and methods for their use are provided herein. According to the embodiments described herein, such antiviral vectors include a full length, replication competent adeno-associated virus (RC AAV).

The term "AAV" may be used to refer to a wild type adeno-associated virus or derivatives thereof, adeno-associated virus subtypes, and naturally occurring and recombinant forms of AAV, unless otherwise indicated. There are about a dozen AAV serotypes, serotype 2 (AAV2) being the most extensively characterized. Other serotypes have been shown to infect specific cell types more effectively than others (e.g., AAV6 is more effective in infecting airway epithelial cells, AAV7 is more effective in infecting murine skeletal muscle cells, AAV8 is more effective in infecting hepatocytes, and AAV1 and AAV5 are more effective at infecting vascular endothelial cells. Recently, more than 100 novel distinct isolates of naturally occurring AAV in human and non-human primate tissues were identified. This led to the use of capsids derived from some of these isolates for pseudotyping, replacing the envelope proteins of AAV2 with the novel envelopes, whereby rAAV2 genomes are then packaged using AAV2 rep and novel capsid genes. Any AAV serotype may be used in accordance with the embodiments described herein, including wild type AAV serotypes (e.g., wild type AAV2), recombinant AAV serotypes or any variants thereof, as long as said serotype is replication competent.

"Recombinant," as applied to a polynucleotide means that the polynucleotide is the product of various combinations of cloning, restriction or ligation steps, and other procedures that result in a construct that is distinct from a naturally-occurring polynucleotide. A recombinant virus is a viral particle comprising a recombinant polynucleotide, including replicates of the original polynucleotide construct and progeny of the original virus construct. An "rAAV vector" or "RC rAAV vector" refers to a recombinant AAV vector that includes a polynucleotide sequence not of AAV origin (i.e., a polynucleotide heterologous to AAV), which may be a sequence of interest for targeting and inhibiting a THV gene. The construction of rAAV vectors carrying particular modifications and the production of rAAV particles, e.g., with modified capsids, is described, e.g., in Shi et al. (2001), Human Gene Therapy 12:1697-1711; Rabinowitz et al. (1999), Virology 265:274-285; Nicklin et al. (2001), Molecular Therapy 4:174-181; Wu et al. (2000), J. Virology 74:8635-8647; and Grifman et al. (2001), Molecular Therapy 3:964-974; the subject matter of which are hereby incorporated by reference as if fully set forth herein.

Typically, rAAV vectors are replication-incompetent because they lack of one or more AAV packaging genes. However, a replication-competent virus (such as the RC rAAVs described herein) refers to a virus that is infectious and capable of being replicated in an infected cell. In the case of AAV, replication competence generally requires the presence of functional AAV packaging genes (e.g., rep and cap). AAV is also a helper-dependent virus, meaning that its replication is also dependent on the presence of a helper virus, also referred to herein as a target helper virus (THV).

A helper virus or a target helper virus (THV) for AAV as used in accordance with the embodiments described herein is a virus that allows AAV to be replicated and packaged by a mammalian cell. The genome of any suitable helper virus for AAV may be targeted, and may include, but are not limited to, genomes of human pathogens such as adenoviruses (AD) (such as Adenovirus type 5 of subgroup C (AD5)), human herpes viruses (HHV) (e.g., herpes simplex viruses 1 and 2 (HSV-1, HSV-2), Epstein-Bar viruses (EBV), and cytomegaloviruses (CMV)), and poxviruses (e.g., vaccinia virus (VV)).

The antiviral vectors described herein may include an inhibitory expression cassette that is inserted into the RC AAV, producing an RC rAAV. According to certain embodiments, the inhibitory expression cassette includes at least one nucleotide sequence that encodes an RNA interference (RNAi) molecule. In one embodiment, the inhibitory expression cassette includes more than one nucleotide sequences that encode an RNA interference (RNAi) molecule. RNAi molecules that are suitable for use in the methods described herein may include small nucleic acid molecules including, but not limited to a short interfering nucleic acid (siNA), a short interfering RNA (siRNA), a double-stranded RNA (dsRNA), a micro-RNA (miRNA), or a short hairpin RNA (shRNA) molecule. According to some embodiments, expression of the at least one RNAi molecule may be under the control of any suitable promoter including, but not limited to, an H1 promoter or a U6 promoter.

In some embodiments, the RNAi molecule targets and binds a complementary nucleic acid sequence that is part of a THV gene which may encode a viral protein. Thus, in some aspects, the THV gene that is targeted by the RNAi molecule may also referred to herein as a "THVi" molecule and the antiviral vectors that include this RNAi molecule are referred to as RC rAAVTHVi vectors. When the RNAi (or THVi) molecule binds the complementary nucleic acid sequence of the THV gene, expression of the THV is inhibited. In one embodiment, the at least one RNAi molecule is an shRNA. In certain aspects, the at least one RNAi molecule is a nucleotide sequence that includes SEQ ID NO:4, SEQ ID NO:5, SEQ ID NO:6, SEQ ID NO:7, SEQ ID NO:8, SEQ ID NO:15, SEQ ID NO:16, SEQ ID NO:17, SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:57, SEQ ID NO:58, SEQ ID NO:59.

THV genes (also sometimes referred as open reading frames, or "ORFs") that may be targeted may include, but are not limited to those in the HPV genome (e.g., capsid proteins L1 and L2, and early region proteins encoded by open reading frames of the early region of the genome E1, E2, E3, E4, E5, E6, E7 and E8); AD genome (e.g., tripartite leader sequence, early transcription units E1A, E1B, E2A, E2B, E3, and E4, intermediate transcription units IVa2 and IX, and late transcription units L1, L2, L3 L4 and L5); herpesvirus genome (e.g., genes that encode conserved viral proteins such as capsid proteins, glycoprotein B, glycoprotein H, glycoprotein L, glycoprotein M, glycoprotein N, helicase-primase ATPase subunit, helicase-primase subunit C, single strand DNA binding protein (e.g., HSV UL29.2), alkaline deoxyribonuclease, deoxyuridine triphoshatase, uracil-DNA glycosidase, ribonucleotide reductase large subunit, maturational protease, assembly protein, capsid transport nuclear protein, terminase ATPase subunit 1, terminase DNA binding subunit 2, terminase binding protein, nuclear egress membrane protein, and nuclear egress lamina protein); and poxvirus genome (e.g. vaccinia viral genome). In some embodiments, the targeted THV gene or nucleotide sequence is HPV E6, HPV E7, AD E1A, AD IVa2, AD Hexon, or AD tripartite leader sequence.

RNAi molecules that may be used in accordance with the methods described herein may include, but are not limited to, RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), or a short hairpin RNA (shRNA) molecule. In one embodiment, the RNAi molecule is an shRNA.

In accordance with some embodiments, the antiviral vectors described above may be used in methods for inhibiting expression of a of a THV gene in a target cell in vivo for treating viral infections or in vitro for cell culture experiments to determine the mechanism of action, efficacy, or other investigative experiments. Such methods may include steps of contacting one or more THV-infected cells (or cells suspected to be infected with a THV) with an antiviral vector which includes an inhibitory expression cassette a nucleotide sequence that encodes an RNAi molecule that inhibits expression of a THV gene, such as those described above.

There are several advantages for designing antiviral RC rAAVTHVi vectors as described herein. First, when co-infected with a targeted helper virus (THV), antiviral RC rAAVTHVi vectors replicate, amplify and potentiate their antiviral effect(s) (Rep and siRNA expression) by increasing DNA template (copy) number and augmentation of antiviral gene expression. Increased siRNA expression is linked to RC rAAVTHVi replication, further inhibiting the targeted helper virus, and increasing the efficacy of even comparatively weak or modest inhibitors. This is in marked contrast to standard non-replicating (NR) rAAVi vectors Additionally, RC rAAVTHVi package and spread to surrounding cells to provide additional protection to both THV infected and uninfected cells during active infection, but due to their replication competence, RC rAAVTHVi retain the ability to integrate and propagate in a cells, so they may be used to latently infect cells and can be challenged with a THV at a later time to provide protection from infection. As such, the vectors may be used as a prophylactic treatment.

Further, antiviral RC rAAVTHVi express the AAV2 Rep protein which possesses additional intrinsic antiviral activity against HPV, and other viruses. For example, AAV2 Rep has been reported to directly bind HPV E7, interfering with its downregulation of the cellular retinoblastoma (Rb) gene, vital to HPV mediated cellular transformation.

Moreover, since Rep mediates AAV2 chromosome 19 site-specific integration into primate DNA, RC rAAVTHVi vectors would likely have a higher safety margin than their Rep-deleted counterparts, which integrate randomly within the genome, while siRNA expression should also be more robust. AAVS1, the preferred integration site for AAV2 in primate cells, has recently been identified as a "safe harbor" for vector integration that promotes sustained transgene expression yet minimizes effects of the vector on surrounding cellular genes and vice versa. However, even in those cells where RC rAAVTHVi doesn't integrate, it will replicate with THV, and then will be either lost or persist as unintegrated RC rAAVTHVi genomes as THV stops replicating.

Methods or Production

In some embodiments, a method for producing an antiviral vector such as those described above is provided. Such a method may include steps for producing RC rAAVTHVi vectors at a high titer. For example, AAV-2 can be propagated both as lytic virus and as a provirus. For lytic growth, AAV requires co-infection with a helper virus. Either adenovirus or herpes simplex can supply helper function. When no helper is available, AAV can persist as an integrated provirus, which involves recombination between AAV termini and host sequences and most of the AAV sequences remain intact in the provirus. The ability of AAV to integrate into host DNA allows propagation absent a helper virus. When cells carrying an AAV provirus are subsequently infected with a helper, the integrated AAV genome is rescued and a productive lytic cycle occurs.

In one embodiment, the method for producing rAAVTHVi vectors at a high titer includes a step of culturing the antiviral vector with a population of cells infected with a first THV, which is a different THV than is targeted by the THVi molecule. Any suitable culture conditions may be used, such as those standard in the art. In such embodiments, the RC rAAVTHVi vectors may be produced at high titer through the use of this different helper virus, because the first THV enables the RC rAAVTHVi to generate a full infectious cycle, which includes integration, replication, packaging, lysis of host cells (e.g., infected human cells or infected cultured cells such as 293 cells), and infection of new cells. In contrast, non-replicative rAAVTHVi vectors, which lack AAV2 Rep and Cap, cannot generate the full infectious cycle.

Culturing the antiviral vector with the infected cells results in a co-infection of the population of cells by both the first THV and the RC rAAVTHVi antiviral vector. Consequentially, the co-infection results in the initiation of the full infectious cycle (i.e., the lytic cycle). After at least one full infectious cycle, the RC rAAVTHVi antiviral vectors produced may be isolated. The ability to generate a full infectious cycle is a tremendous advantage for RC rAAVTHVi vectors, and may result in a 2-4 log difference in vector production over their non-replicative (NR) counterparts. Ultimately, larger vector stocks would simplify vector packaging, and increase the pool of potential patients for which a therapeutic RC rAAVTHVi vector could be used.

The method may also include a step of isolating or purifying the antiviral vector after at least one full infectious cycle. Isolating or purifying the antiviral vector may be accomplished by any suitable method known in the art. One skilled in the art would understand how to propagate and isolate AAV.

Pharmaceutical Compositions

According to some embodiments, the antiviral vectors described herein may be part of a pharmaceutical composition. Such a pharmaceutical composition may include one or more antiviral vector and a pharmaceutically acceptable carrier. In some embodiments, the pharmaceutical composition may include a single type of antiviral vector, or alternatively, may include more than one type of antiviral vector. For example, the pharmaceutical composition may include an antiviral vector that includes a first RNAi molecule that targets a first THV gene, or it may include additional antiviral vectors that that includes a second RNAi molecule that targets target a second THV gene, and so on.

A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid, solid, or semi-solid filler, solvent, surfactant, diluent, excipient, adjuvant, binder, buffer, dissolution aid, solvent, encapsulating material, sequestering agent, dispersing agent, preservative, lubricant, disintegrant, thickener, emulsifier, antimicrobial agent, antioxidant, stabilizing agent, coloring agent, or some combination thereof.

Each component of the carrier is "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) natural polymers such as gelatin, collagen, fibrin, fibrinogen, laminin, decorin, hyaluronan, alginate and chitosan; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as trimethylene carbonate, ethyl oleate and ethyl laurate; (13) agar; (14) buffering agents, such as magnesium hydroxide and aluminum hydroxide; (15) alginic acid (or alginate); (16) pyrogen-free water; (17) isotonic saline; (18) Ringer's solution; (19) alcohol, such as ethyl alcohol and propane alcohol; (20) phosphate buffer solutions; (21) thermoplastics, such as polylactic acid, polyglycolic acid, (22) polyesters, such as polycaprolactone; (23) self-assembling peptides; and (24) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of antiviral vectors in these formulations can vary widely, and will be selected primarily based on fluid volumes, viscosities, organ size, body weight and the like in accordance with the particular mode of administration selected and the biological system's needs.

Therapeutic Uses of Antiviral Vectors and Pharmaceutical Compositions Thereof

According to the embodiments described herein, an antiviral vector or a pharmaceutical composition thereof may be used to kill a target cell that is infected with a THV. The target cell may be part of an in vitro cell culture population or may be part of an in vivo tissue or organ found in a subject. When the target cell is part of an in vitro cell culture population, the antiviral vectors may be used as a preclinical research tool to investigate a novel antiviral vector's mechanism of action, efficacy, ability to target and eradicate a THV infection, ability to prevent a THV infection, or ability to inhibit expression of a viral protein associated a THV infection.

When the target cell is part of an in vivo tissue or organ found in a subject, the antiviral vector or pharmaceutical composition thereof may be used in a method to treat or prevent a THV infection in a subject. Such methods may include a step of administering a therapeutically effective amount of one or more antiviral vectors (such as those described above) or a pharmaceutical composition thereof. Antiviral vectors that may be used in accordance with the methods described herein may include a replication competent AAV virus inserted with an RNAi molecule that inhibits expression of a viral protein associated with the THV, such as any of the AAV vectors described above. In some embodiments, the methods may include administering more than one type of antiviral vectors to the subject. For example, the method may include administration of an antiviral vector that includes a first RNAi molecule that targets a first THV gene, or it may include administration of additional antiviral vectors that that include a second RNAi molecule that target a second THV gene, and so on.

Viral infections that may be treated or prevented in accordance with the methods described herein may include, but are not limited to, active viral infections in an otherwise healthy subject or host, or opportunistic infections that occur in an immune compromised or immunosuppressed subject or host.

As described above, adeno-associated virus (AAV) is a nonpathogenic virus that requires helper functions from another virus (i.e., a THV) for productive (lytic) infection. Table 1 below shows target helper viruses and their related infections that may be targeted, treated and/or prevented by the vectors described herein.

TABLE 1

| | | THV infections | |
|---|---|---|---|
| VIRUS FAMILY | SPECIES | INFECTION IN HEALTHY HOST | INFECTION IN IMMUNOSUPPRESSED HOST |
| Adenovirus (Ad) | There are at least 57 human Ad types (HAdV-1 to 57) in seven species (Ad-A, Ad-B, Ad-C, Ad-D, Ad-E, Ad-F, Ad-G) | Upper respiratory tract infections (e.g., tonsillitis, ear infection, croup, bronchitis, pneumonia); gastroenteritis, | Upper respiratory tract infections (e.g., tonsillitis, ear infection, croup, bronchitis, pneumonia); gastroenteritis, |

TABLE 1-continued

THV infections

| VIRUS FAMILY | SPECIES | INFECTION IN HEALTHY HOST | INFECTION IN IMMUNOSUPPRESSED HOST |
|---|---|---|---|
| Human Herpes Viruses (HHV) | Herpes simplex virus 1 (HSV-1/HHV-1) Herpes simplex virus 2 (HSV-2/HHV-2) Varicella zoster virus (VSV/HHV-3) Epstein-Barr virus (EBV/HHV-4) Cytomegalovirus (CMV/HHV-5) HHV-6A/HHV-6B and HHV-7 Kaposi's Sarcoma-associated herpesvirus (KSHV/HHV-8) | Oral and/or genital herpes, as well as other herpes simplex infections Chicken pox and shingles Infectious mononucleosis, Burkitt's lymphoma, Infectious mononucleosis-like syndrome, eye infections, disseminated disease, urinary infections Roseola infantum Generally dormant | Recurrent, disseminated papules, hepatitis, pneumonia, CNS infections Localized to disseminated papular lesions, pneumonia, hepatitis Infectious mononucleosis, disseminated infection, CNS lymphoma in AIDS patients, post-transplant lymphoproliferative syndrome, HIV-associated hairy leukoplakia Infectious mononucleosis-like syndrome, eye infections, disseminated disease, urinary infections Have part of AAV inserted into the viral genome Kaposi's sarcoma in patients with AIDS, primary effusion lymphoma, multicentric Castelman's disease |
| Human Papillomavirus Virus (HPV) | Over 120 HPV types have been identified | Genital and hand/foot warts and papillomas, genital or oropharyngeal cancers (e.g., cervical, vulvar, penile, anal), Disseminated Disease | Genital and hand/foot warts and papillomas, genital or oropharyngeal cancers (e.g., cervical, vulvar, penile, anal), Disseminated Disease |
| Poxvirus | Vaccinia virus | Skin infections, disseminated disease | Skin infections, disseminated disease |

AAV is capable of infecting a wide variety of animal cells, and tissues. It also infects cells in stationary phase. In practice, one skilled in the art would understand that the vectors described herein may be used to target any helper virus. Other non-helper viruses may be targeted as well.

From a Biosafety standpoint, the RC rAAVTHVi antiviral vectors should be no more toxic than wild type AAV2, which is considered a nonpathogen by the CDC, assuming that the expressed siRNAs are themselves not toxic. Like wild type AAV2, RC rAAVTHVi vectors would not be capable of replicating independently, but would still require adenovirus or another "helper" virus for replication.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, a treatment with an antiviral vector or a pharmaceutical composition thereof may be used to treat or prevent an active viral infection in an otherwise healthy subject, or may be used to prevent or treat a viral infection in an immuocompromised or immunosuppressed patient who is a greater risk for infection (e.g., marrow transplant patients, chemotherapy patients, HIV patients). The treatments described herein may be used in any suitable subject, including a human subject or any mammalian or avian subject that needs treatment in accordance with the methods described herein (e.g., dogs, cats, horses, rabbits, mice, rats, pigs, cows).

An antiviral vector or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration. In one embodiment, the MTPs or a pharmaceutical composition thereof is administered parenterally. A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

An antiviral vector or a pharmaceutical composition thereof can be given to a subject in the form of formulations or preparations suitable for each administration route. The formulations useful in the methods of the invention include one or more antiviral vectors, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of an antiviral vector, which can be combined with a carrier material to produce a pharmaceutically effective dose, will generally be that amount of an antiviral vector which produces a therapeutic effect.

Methods of preparing these formulations or compositions include the step of bringing into association an antiviral vector with one or more pharmaceutically acceptable carriers and, optionally, one or more accessory ingredients. In general, the formulations are prepared by uniformly and intimately bringing into association an antiviral vector with liquid carriers, or finely divided solid carriers, or both.

Formulations suitable for parenteral administration comprise an antiviral vector in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents, viscous agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In an embodiment of the invention, an antiviral vector or composition thereof is delivered to a disease or infection site in a therapeutically effective dose. A "therapeutically effective amount" or a "therapeutically effective dose" is an amount of an antiviral vector that produces a desired therapeutic effect in a subject, such as preventing or treating a target condition or alleviating symptoms associated with the condition. The most effective results in terms of efficacy of treatment in a given subject will vary depending upon a variety of factors, including but not limited to the characteristics of the antiviral vector, the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

In contrast to currently available rAAV vectors, the examples described below utilize full length wild type AAV (RC rAAV) inserted with inhibitory siRNA cassettes targeting specific helper viruses. These vectors also encode the AAV Rep protein. Wild type AAV is a well known inhibitor of helper virus replication (including Ad and HPV replication) through the action of AAV encoded Rep function(s), and potentially the actions of its inverted terminal repeats (ITRs). As discussed herein, there are several advantages to designing RC rAAVs as described herein. (1) When co-infected with a targeted helper virus (THV), antiviral RC rAAVTHVi vectors replicate, amplify and potentiate their antiviral effect(s) by increasing DNA template number and augmentation of antiviral gene expression. In contrast, standard AAV Rep/Cap deficient (NR) rAAVTHVi vectors cannot replicate, and require a larger amount of vector for the same level of inhibition. (2) During active infection, RC rAAVTHVi package and spread to surrounding cells to provide additional protection to both THV infected and uninfected cells. (3) Antiviral RC rAAVTHVi express the AAV2 Rep protein which possesses additional intrinsic antiviral activity against HPV, and other viruses. (4) RC rAAVTHVi vectors would be easier to produce at high titer using a different or irrelevant "helper" virus than the THV, because they can generate a full infectious (or lytic) cycle within helper virus infected cells (e.g., 293 cells), while NR rAAVTHVi vectors cannot. (5)

Example 1: Design of RNAi Molecules

Starting from a target mRNA or DNA sequence (sense), a plurality of complementary sequences of siRNA guide strands (antisense) are generated and the complementary target mRNA or DNA sequences are evaluated for their potential efficacy. The guide strands are generally between approximately 18 and 25 nucleotides in length, but may be shorter or longer in accordance with some embodiments. In certain embodiments, the guide strands are 19, 20 or 21 nucleotides in length.

The guide strands may be randomly screened to determine their efficacy, however, in some embodiments, an algorithm or a set of rules may then applied to the guide strands to eliminate strands with unwanted motifs or potential off-target effects, and may include a score to determine the potency or efficacy of each eventual RNAi molecule's (siRNA or shRNA) ability to bind to its target sequence. Any suitable algorithm or set of rules may be used to select one or more siRNA molecules. Many algorithms for siRNA or shRNA design exist including, but not limited to, computer-assisted algorithms and algorithms published by Rossi, Shabalina, Saetrom, Takasaki, Hsieh, Tuschl, Reynolds, Ui-Tei, Amarzguioui and others (see Amazguioui & Prydz 2004; Amazguioui et al. 2006; Castanotto et al. 2002; Hsieh et al. 2004; Kim et al. 2004; Kim et al. 2005; Lee et al. 2002; Reynolds et al. 2004; Saetrom & Snove 2004; Shabalina et al. 2006; Takasaki et al. 2004; Ui-Tei et al. 2004, the subject matter of which is hereby incorporated by reference as if fully set forth herein).

Alternatively, in some embodiments, a new or unique algorithm may be designed based on rational siRNA design rules, guidelines known in the art, or modifications thereof. For example, criteria that may be applied to evaluate the efficacy of a potential target sequence (sense) may include, but are not limited to, length of the functional siRNAs, GC content of the functional siRNA, thermodynamic end stability of the antisense strand, avoidance of tandem repeats and palindromes, target mRNA accessibility, structural features, and additional position specific determinants.

Once a set of candidate siRNA molecules and their target sequences have been selected, they may be used in accordance with the embodiments described herein to produce shRNA molecules for expression by an expression cassette that is part of an RC rAAV. In the embodiments described herein, an shRNA molecule includes an antisense sequence of approximately 19 or more nucleotides, a loop sequence of approximately 3-23 nucleotides, a complementary sense sequence, and a terminal sequence of approximately 4-6 Uracils or Thymines. Optionally a leader sequence and/or a trailer sequence may be included. Evaluation of shRNA molecules according to some embodiments is described further in the Examples below.

Example 2: Inhibition of HPV E6 and E7 Genes shRNA molecules that inhibit the HPV E6 and E7 genes and that may be used in RC AAV antiviral vectors in accordance with the embodiments described herein were designed using different algorithms.

Rossi Algorithm

Using an algorithm published by Rossi ("the Rossi Algorithm") a set of target sequences that are part of HPV31b's early genome transcript that encodes viral proteins E6 and E7 (E6/7) were identified (FIG. 1). shRNA inhibitors of E6/7 were generated against the target sequences. Table 2 shows the target sequences that correspond to each of the E6/7 inhibitors (sh1, sh2, sh3, sh4 and sh5).

TABLE 2

Target sequences on HPV31b selected using Rossi Algorithm

| HPV31b E6/7 INHIBITOR NAME | TARGET SEQUENCE | SEQ ID NO |
|---|---|---|
| sh1 | CTGCAGAAAGACCTCGGAAA | 42 |
| sh2 | GGACGACACACCACACGGAGT | 43 |
| sh3 | GAGAAGACCTCGTACTGAA | 44 |
| sh4 | CCACACGGAGTGTGTACAAA | 45 |
| sh5 | GAGCAATTACCCGACAGCTCA | 46 |

The shRNA inhibitors of E6/7 which correspond to the target sequences above are shown in Table 3 (below) and FIG. 2 (sense sequence is in BOLD, loop sequence in italics, and antisense sequence is UNDERLINED):

TABLE 3 shRNA inhibitors of E6/7 designed based on the Rossi Algorithm

| HPV31b E6/7 INHIBITOR NAME | shRNA SEQUENCE | SEQ ID NO |
|---|---|---|
| sh1 (HPV31-shRNA1) | 5'GTGGAAAGGACGAAACACCGCTGCAGAAAG ACCTCGGAAAtttgtgtagTTTCCGAGGTCTTTCT GCAGTTTTTGATATCAAGT3' | 4 |

TABLE 3-continued shRNA inhibitors of E6/7 designed based on the Rossi Algorithm

| HPV31b E6/7 INHIBITOR NAME | shRNA SEQUENCE | SEQ ID NO |
|---|---|---|
| sh2 (HPV31-shRNA2) | 5'GTGGAAAGGACGAAACACCGGACGACACA CCACACGGAGTttcaagagaACTCCGTGTGGTGT GTCGTCCTTTTTGATATCAAGT3' | 5 |
| sh3 (HPV31-shRNA3) | 5'GTGGAAAGGACGAAACACCGAGAAGACCTC GTACTGAAtttgtgtagTTCAGTACGAGGTCTTCTC TTTTTGATATCAAGT3' | 6 |
| sh4 (HPV31-shRNA4) | 5'GTGGAAAGGACGAAACACCGCCACACGGA GTGTGTACAAAtttgtgtagTTTGTACACACTCCGT GTGGTTTTTGATATCAAGT3' | 7 |
| sh5 (HPV31-shRNA5) | 5'GTGGAAAGGACGAAACACCGAGCAATTACC CGACAGCTCAtttgtgtagTGAGCTGTCGGGTAAT TGCTCTTTTTGATATCAAGT3' | 8 |

Figure 3A:
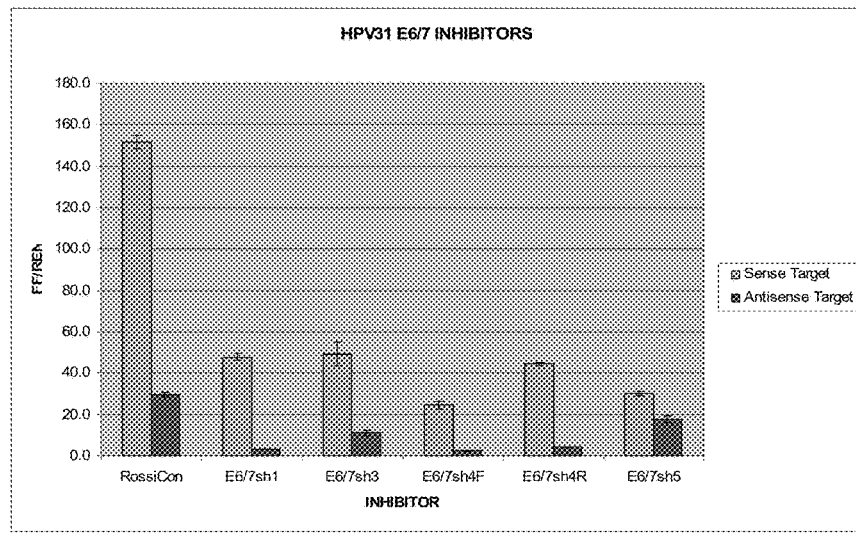
FIGS. 3A-B illustrate the efficacy of inhibitors targeting HPV31b E6/7 loci using a dual luciferase assay. Inhibition is measured as the ratio of light emitted from the firefly and renilla luciferase reactions (FF/REN).
Figure 3B:
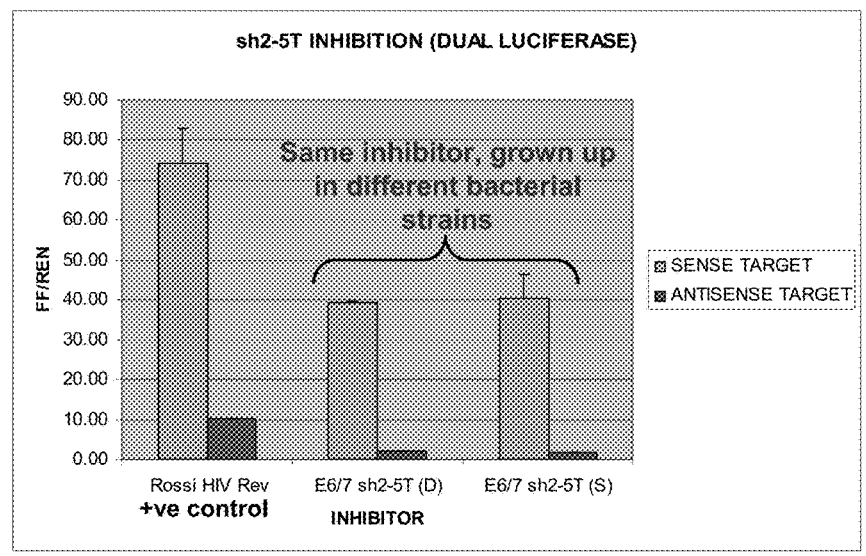

The efficacy of the Rossi Algorithm-derived HPV31b E6/7 inhibitors was evaluated by cloning each of the target sequences into a 3'UTR region of Renilla Luciferase and measuring inhibition as the ratio of light emitted from the firefly and renilla luciferase reactions (FIGS. 3A and 3B). The sh2 inhibitor (which targets the E6 intron) was determined to be the best inhibitor (FIG. 3B).

Shabalina Algorithm

Figure 4:
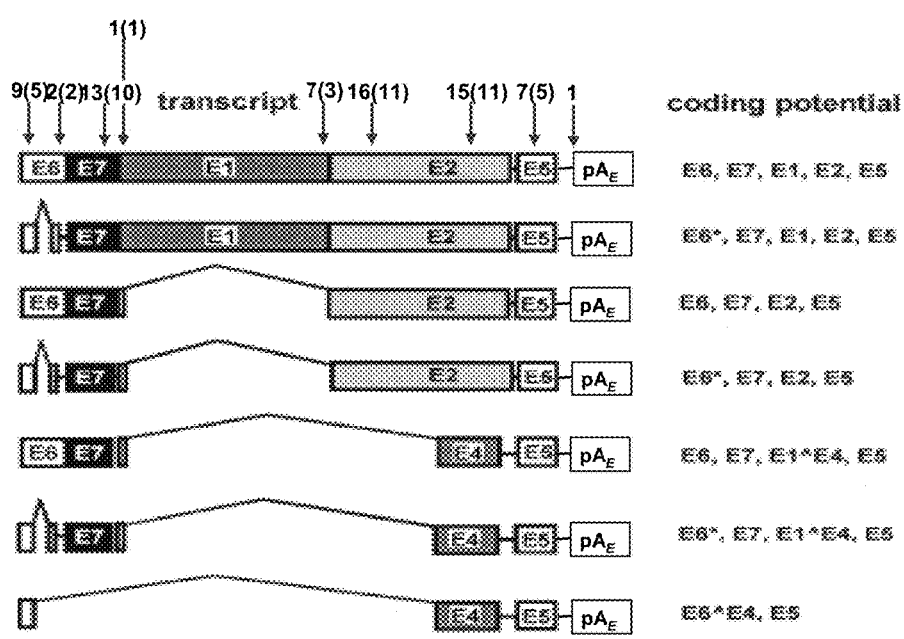
FIG. 4 is a graphic representation of target HPV31b sequences using the Shabalina Algorithm. Brackets indicate more stringent thermodynamic stability. As the figure shows, some of the less stringent targets are near the recommended range (e.g., the poly-A target). The sequences at the terminus of E1 are in the sequence after the intron, immediately upstream of E2, as E1 extends into E2.
Figure 7:
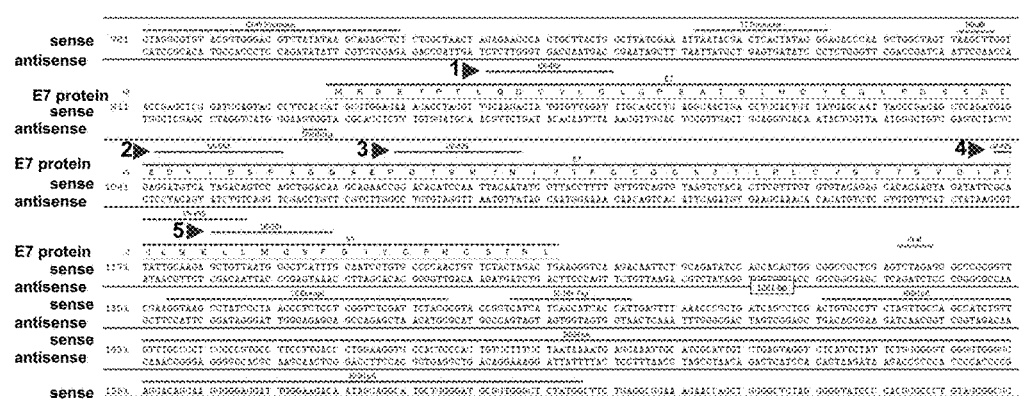
Figure 9:
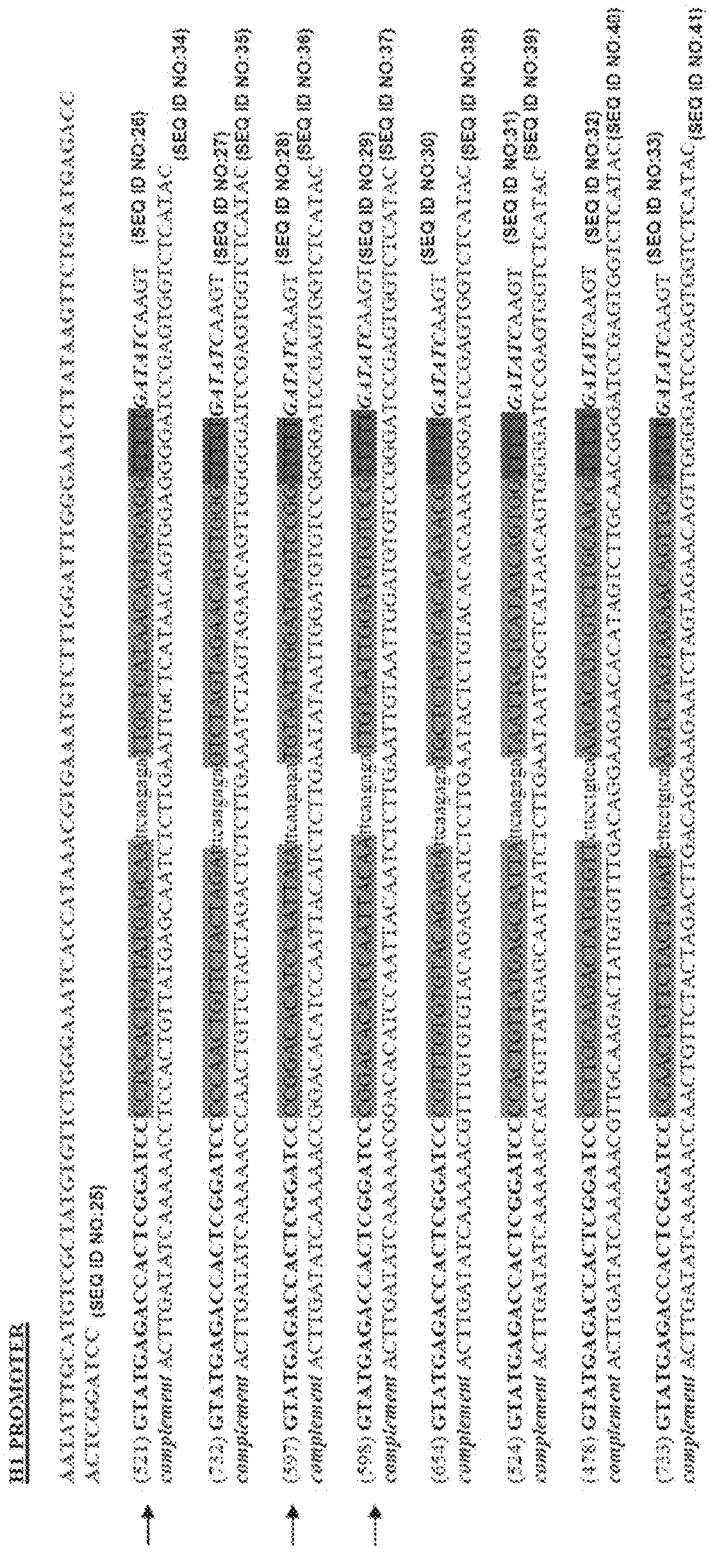
FIG. 9 shows the sequences of the H1 promoter (SEQ ID NO:25) and the shRNA HPV E7 inhibitors (and complement sequences) designed using the Shabalina Algorithm. (SEQ ID NOs:26-41). Arrows indicate inhibitors that showed the greatest activity against E7 target gene.

Using an algorithm published by Shabalina ("the Shabalina Algorithm") a set of target sequences that are part of the HPV31b early genome transcript were identified (FIGS. 4, 5 and 7). The thirteen E7 target sequences corresponding to E7 target sequences coordinates 478, 482, 521, 524, 563, 597, 598, 599, 654, 688, 701, 732, and 733 (FIG. 5) were used to design shRNA E7 inhibitors using one of two promoters, H1 or U6. The shRNA E7 inhibitors are shown in Table 4 (below) and FIGS. 6 and 9 (sense sequence is in BOLD, loop sequence in italics, and antisense sequence is UNDERLINED):

TABLE 4 shRNA inhibitors of E7 designed based on the Shabalina Algorithm

| HPV31b E7 INHIBITOR NAME | shRNA SEQUENCE | PROMOTER | SEQ ID NO |
|---|---|---|---|
| H1shE7 (478) | GTATGAGACCACTCGGATCCCCGTTGCA AGACTATGTGTTcttcctgtcaAACACATAGT CTTGCAACGTTTTTGATATCAAGT | H1 | 32 |
| U6shE7 (482) | GTGGAAAGGACGAAACACCGCAAGACT ATGTGTTAGATttcaagagaATCTAACACAT AGTCTTGCTTTTTGATATCAAGT | U6 | 15 |
| H1shE7 (521) | GTATGAGACCACTCGGATCCCCTCCAC TGTTATGAGCAAttcaagagaTTGCTCATA ACAGTGGAGGTTTTTGATATCAAGT | H1 | 26 |
| H1shE7 (524) | GTATGAGACCACTCGGATCCCCACTGT TATGAGCAATTAttcaagagaTAATTGCTC ATAACAGTGGTTTTTGATATCAAGT | H1 | 31 |
| U6shE7 (563) | GTGGAAAGGACGAAACACCGGATGTCA TAGACAGTCTAttcaagagaTGGACTGTCT ATGACATCCTTTTTGATATCAAGT | U6 | 16 |

TABLE 4-continued shRNA inhibitors of E7 designed based on the Shabalina Algorithm

| HPV31b E7 INHIBITOR NAME | shRNA SEQUENCE | PRO-MO-TER | SEQ ID NO |
|---|---|---|---|
| H1shE7 (597) | GTATGAGACCACTCGGATCCCCGGACA CATCCAATTAttcaagagaTGTAATTGGAT GTGTCCGGTTTTTGATATCAAGT | H1 | 28 |
| H1shE7 (598) | GTATGAGACCACTCGGATCCCGGACAC ATCCAATTACAAttcaagagaTTGTAATTG GATGTGTCCGTTTTTGATATCAAGT | H1 | 29 |
| U6shE7 (599) | GTGGAAAGGACGAAACACCGGACACAT CCAATTACAATttcaagagaATTGTAATTG GATGTGTCCTTTTTGATATCAAGT | U6 | 17 |
| H1shE7 (654) | GTATGAGACCACTCGGATCCCGTTTGT GTGTACAGAGTAttcaagagaTGCTCTGTA CACACAAACGTTTTTGATATCAAGT | H1 | 30 |
| U6shE7 (688) | GTGGAAAGGACGAAACACCGCATATTG CAAGAGCTGTTcttcctgtcaAACAGCTCTT GCAATATGCTTTTTGATATCAAGT | U6 | 18 |
| U6shE7 (701) | GTGGAAAGGACGAAACACCGCTGTTAA TGGGCTCATTTcttcctgtcaAAATGAGCCC ATTAACAGCTTTTTGATATCAAGT | U6 | 19 |
| H1shE7 (732) | GTATGAGACCACTCGGATCCCCCAACT GTTCTACTAGAttcaagagaGTCTAGTAGA ACAGTTGGGTTTTTGATATCAAGT | H1 | 27 |
| H1shE7 (733) | GTATGAGACCACTCGGATCCCCAACTG TTCTACTAGATTcttcctgtcaAGTCTAGTAG AACAGTTGGTTTTTGATATCAAGT | H1 | 33 |

Figure 8:
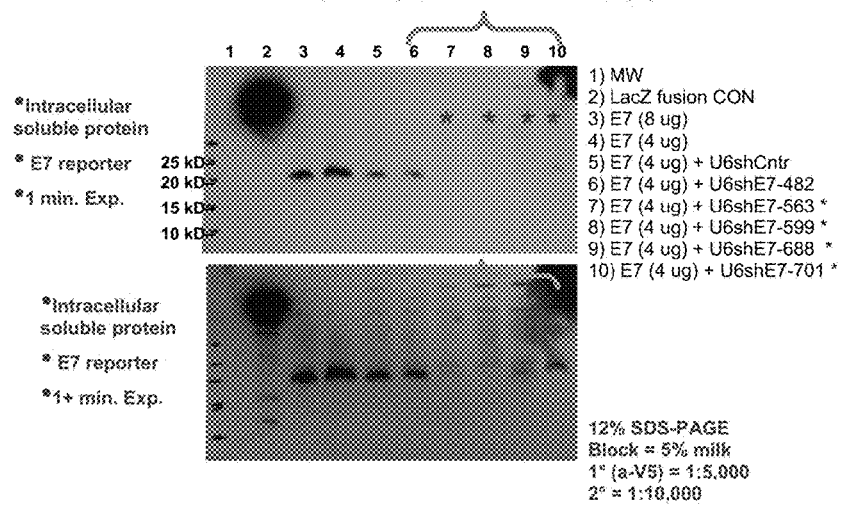
FIG. 8 is a gel electrophoresis (12% SDS-PAGE) illustrating a U6-driven HPV31 b E7 shRNA inhibitor screen against E7-V5 Tagged expressor. Lane 1. MW marker, Lane 2. LacZ. Lanes 3-5, E7 Controls. Lanes 6-10, HPV31 E7 Target+U6siRNAE7s. The target is expressed in Lane 6, but not in Lanes 7-10, indicating the destruction of the target E7. Each siRNA targets a specific region of the HPV31 E7 gene (see FIG. 7)
Figure 10:
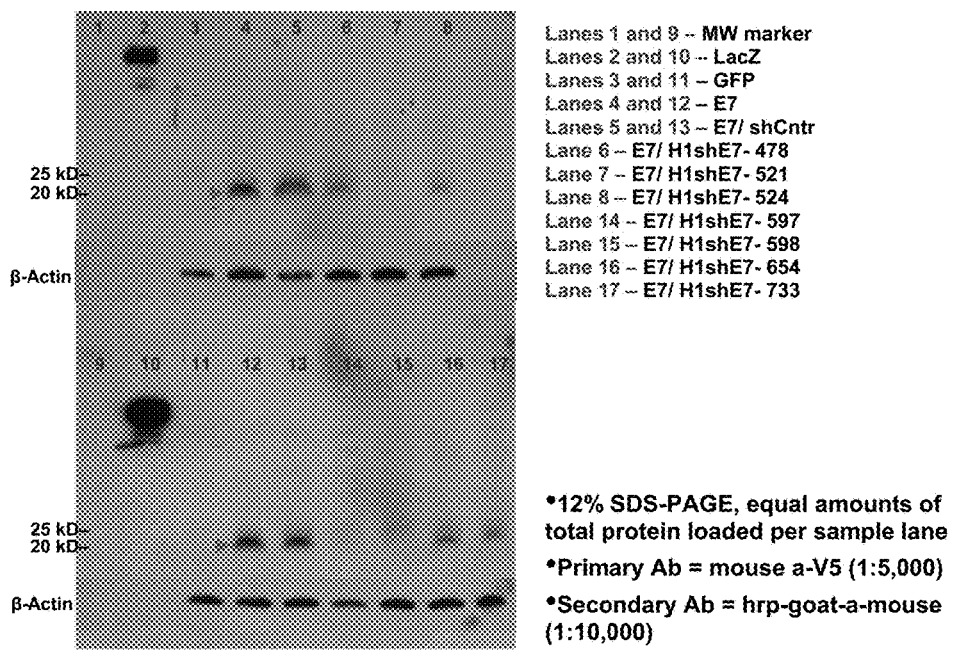
FIG. 10 is a gel electrophoresis (12% SDS-PAGE) illustrating a H1-driven HPV31b E7 shRNA inhibitor screen against E7-V5 Tagged expressor. Lanes 7, 14 and 15-10 show the strongest inhibition of E7 by the corresponding shRNA inhibitors.

Expression of the HPV31 E7 gene—which is a gene essential to HPV replication—was most effectively inhibited by U6shE7(563), U6shE7(599), U6shE7(688), U6shE7(701), H1shE7(521), H1shE7(597) and H1shE7(598) (see FIGS. 8 and 10). Table 5 below shows the target sequences that correspond to each of the HPV31 E7 inhibitors shown to be effective.

TABLE 5

Effective target sequences on HPV31 selected using Shabalina Algorithm

| HPV31b E7 ORF INHIBITOR NAME | TARGET SEQUENCE | SEQ ID NO: |
|---|---|---|
| shE7(521) | CCTCCACTGTTATGAGCAA | 47 |
| shE7(563) | GGATGTCATAGACAGTCCA | 48 |
| shE7(597) | CCGGACACATCCAATTACA | 49 |
| shE7(598) | CGGACACATCCAATTACAA | 50 |
| shE7(599) | GGACACATCCAATTACAAT | 51 |
| shE7(688) | GCATATTGCAAGAGCTGTT | 52 |
| shE7(701) | GCTGTTAATGGGCTCATTT | 53 |

Example 3: Inhibition of Adenoviral Genes shRNA inhibitors of E1A, IVa2, and Hexon Adenoviral (AD5) genes, were expressed as previously described (Eckstein et al. 2010). Table 6 shows the target sequences that correspond to each of the AD5 Target genes used to produce the shRNA inhibitors.

TABLE 6

Target sequences on AD5 based on Eckstein et al. 2010)

| AD5 GENE TARGET | AD5 INHIBITOR NAME | AD5 GENE TARGET SEQUENCE (sense) | SEQ ID NO: |
|---|---|---|---|
| E1A | siE1A-4 | CGGAGGTGTTATTACCGAA | 54 |
| IVa2 | siIVa2-2 | GTTAGTGATCCCAGAAATA | 55 |
| Hexon | siHexon-4 | GCTAGAAAGTCAAGTGGAA | 56 |

The sense and antisense sequences of the shRNA AD5 gene target inhibitors are shown in Table 7 below (sense sequence is in BOLD, loop sequence $\{x_{4-10}\}$, and antisense sequence is UNDERLINED):

TABLE 7 shRNA inhibitors based on Eckstein et al. 2010

| AD5 INHIBITOR NAME | shRNA SEQUENCE | SEQ ID NO |
|---|---|---|
| shE1A-4 | CGGAGGTGTTATTACCGAA-$\{x_{4-10}\}$-UUCGGUAAUAACACCUCC | 57 |
| shIVa2-2 | GTTAGTGATCCCAGAAATA-$\{x_{4-10}\}$-UAUUUCUGGGAUCACUAAC | 58 |
| shHexon-4 | GCTAGAAAGTCAAGTGGAA-$\{x_{4-10}\}$-UUCCACUUGACUUUCUAGC | 59 |

Figure 12A:
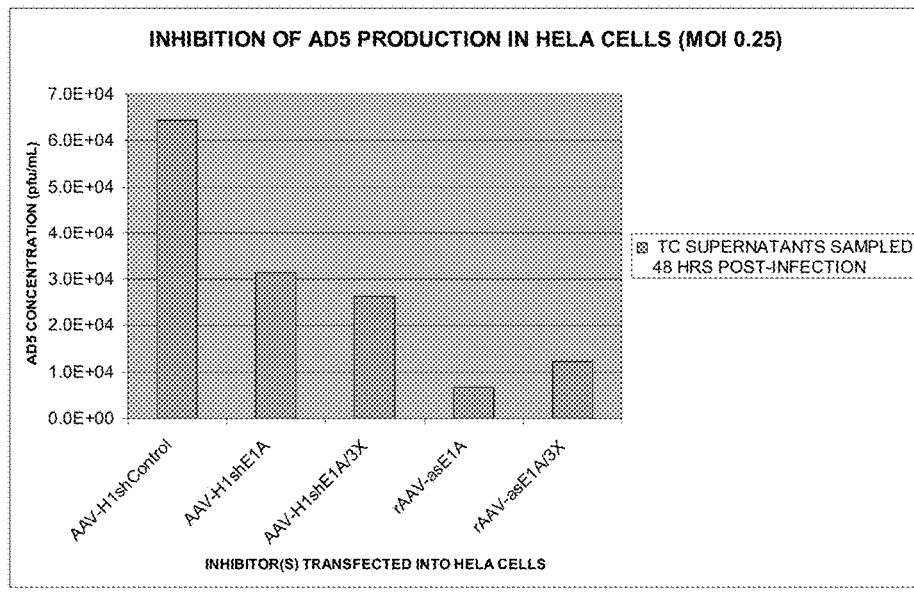
FIGS. 12A-B show the results of challenge assays using a new AD5 titer and performed on HeLa cells. Plaques were read on Vero cells.
Figure 12B:
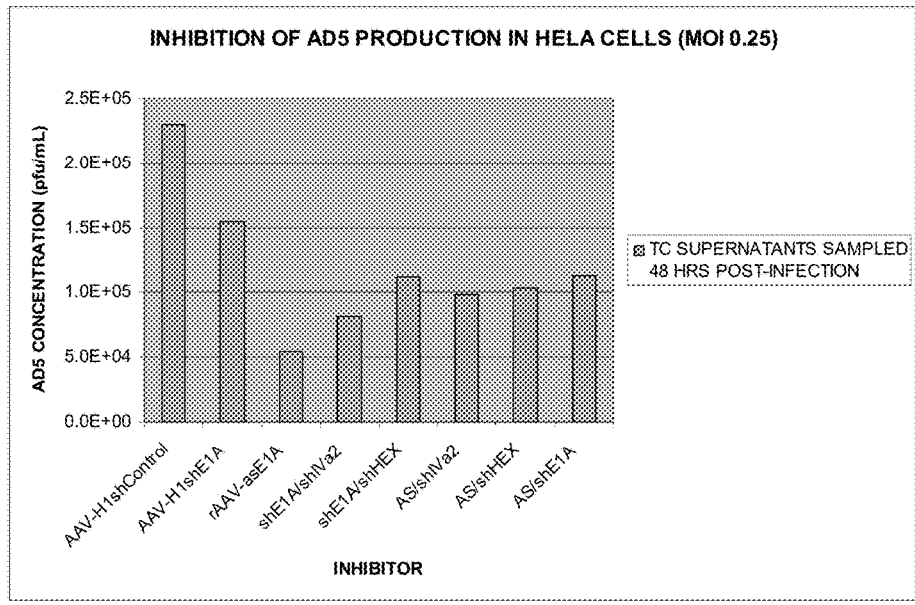

As shown in FIGS. 12A and 12B, when transfected into HeLa cells infected with AD5, the Ad5 inhibitors (shE1A-4, shIVa2-2 and shHexon-4) were able to inhibit the production of AD5 as compared to a control.

Figure 11:
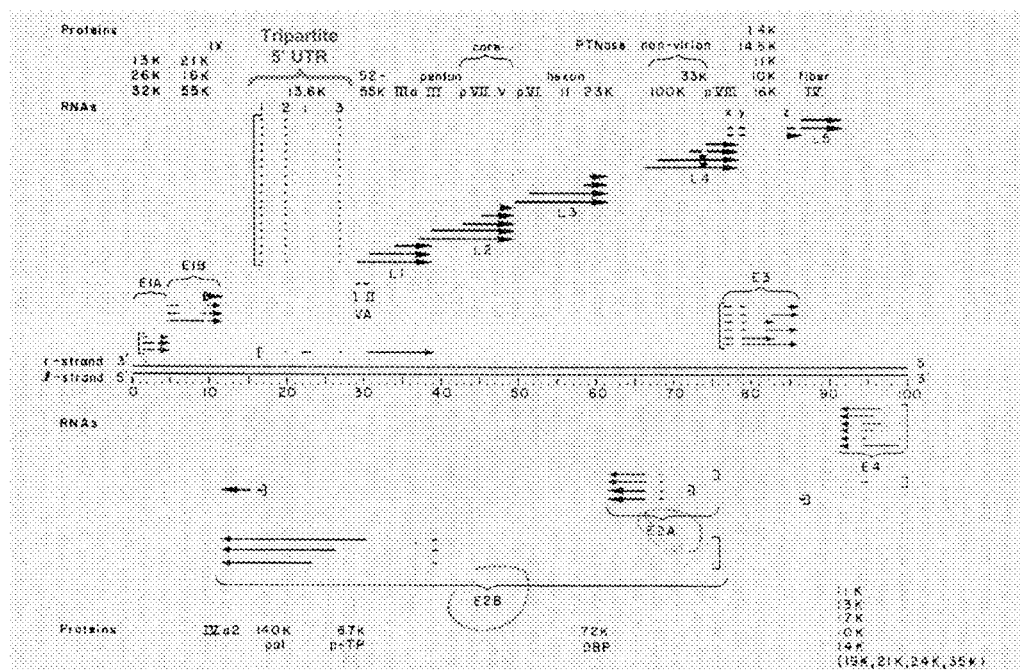
FIG. 11 shows the position of the Adenovirus Tripartite Leader Sequence (Tripartite 5' UTR) in relation to the other Adenoviral genes.

Using the Shabalina Algorithm, a set of target sequences that are part of the Adenoviral (AD5) Tripartite Leading Sequence (TriP) were identified (FIG. 11). Table 8 shows the target sequences that correspond to each of the AD5 Target genes used to produce shRNA or siRNA inhibitors.

TABLE 8

Target sequences on AD5 TriP selected using the Shabalina Algorithm

| AD INHIBITOR NAME | TARGET SEQUENCE (sense) | SEQ ID NO: |
|---|---|---|
| TriP(45) | CGGAGGTGTTATTACCGAA | 60 |
| TriP(46) | GTTAGTGATCCCAGAAATA | 61 |
| TriP(170) | GCTAGAAAGTCAAGTGGAA | 62 |

REFERENCES

The references, patents and published patent applications listed below, and all references cited in the specification above are hereby incorporated by reference in their entirety, as if fully set forth herein.

Amarzguioui, M. & Prydz, H. (2004). An algorithm for selection of siRNA sequences. *Biochem, Biophys. Res. Commun.*, 316, 1050-1058.

Amarzguioui M. Lundberg P. Cantin E. Hagstrom J. Behlke A. M. Rossi J. J., (2006) Rational design and in vitro and in vivo delivery of Dicer substrate siRNA, Nat. Protocols, P 508-P 517

Castanotto D, Li H, Rossi J J. (2002) Functional siRNA expression from transfected PCR products. RNA 8: 1454-60.

Eckstein A., et al. (2010) Inhibition of adenovirus infections by siRNA-mediated silencing of early and late adenoviral gene functions, Antiviral Research 88:86-94.

Hsieh A C, Bo R, Manola J, Vazquez F, Bare O, Khvorova A, Scaringe S, Sellers W R. A library of siRNA duplexes targeting the phosphoinositide 3-kinase pathway: determinants of gene silencing for use in cell-based screens. Nucleic Acids Res. (2004) 32:893-901. doi: 10.1093/nar/gkh238.

Kim D. H.; M. Longo; Y. Han; P. Lundberg; E. Cantin; and J. J. Rossi. "Interferon induction by siRNAs and ssRNAs synthesized by phage polymerase." Nat Biotechnol, 22: 321-325, March 2004.

Kim H. D. Behlke A. M. Rose D. S. Chang S. M. Choi S. Rossi J. J., (2005) Synthetic dsRNA Dicer substrates enhance RNAi potency and efficacy, Nat. Biotechnol., P 222-P 226

Lee N S, Dohjima T, Bauer G, Li H, Li M-J, Ehsani A, Salvaterra P, Rossi J. (2002) Expression of small interfering RNAs targeted against HIV-1 rev transcripts in human cells. Nature Biotechnology 20: 500-5.

Reynolds, A., Leake, D., Boese, Q., Scaringe, S., Marshall, W. S. & Khvorova, A. (2004). Rational siRNA design for RNA interference. Nat. Biotechnol. 22:326-330.

Saetrom P, Snove O J. A comparison of siRNA efficacy predictors. Biochem Biophys Res Commun. (2004) 321: 247-253.

Shabalina S A, Spiridonov A N, Ogurtsov A Y (2006). Computational models with thermodynamic and composition features improve siRNA design. BMC Bioinformatics, 7, 65.

Takasaki S, Kotani S, Konagaya A. An effective method for selecting siRNA target sequences in mammalian cells. Cell Cycle. (2004) 3:790-795.

Ui-Tei, K., Naito, Y., Takahashi, F., Haraguchi, T., Ohki-Hamazaki, H., Juni, A., Ueda, R. & Saigo, K. (2004). Guidelines for the selection of highly effective siRNA sequences for mammalian and chick RNA interference, Nucleic Acids Res., 32, 936-948.

What is claimed is:

1. A pharmaceutical composition comprising:
(i) one or more antiviral vectors, each comprising an inhibitory expression cassette; and a replication competent adeno-associated virus (AAV); and
(ii) a pharmaceutically acceptable carrier,
wherein the inhibitory expression cassette comprises a nucleotide sequence that encodes an RNAi molecule that inhibits expression of a targeted helper virus (THV) gene, and
wherein the RNAi molecule is an shRNA comprising a sequence selected from the group consisting of SEQ ID NO:4, SEQ ID NO:5, SEQ ID NO:6, SEQ ID NO:7, SEQ ID NO:8, SEQ ID NO:15, SEQ ID NO:16, SEQ ID NO:17, SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:57, SEQ ID NO:58, and SEQ ID NO:59.

2. The pharmaceutical composition of claim 1, wherein the inhibitory expression cassette further comprises an H6 or U6 promoter.

3. The pharmaceutical composition of claim 1, wherein the THV gene is part of an Adenovirus (Ad) genome, a Human Papillomavirus (HPV) genome, a Human Herpes Virus (HHV) genome, or a Vaccinia virus (VV) genome.

4. The pharmaceutical composition of claim 3, wherein the THV gene is HPV E6 or HPV E7.

5. The pharmaceutical composition of claim 3, wherein the THV gene is Ad E1, Ad IVa, or Ad Hexon.

6. The pharmaceutical composition of claim 3, wherein the RNAi molecule targets Ad Tripartite Leader Sequence (TriP).

7. The pharmaceutical composition of claim 1, wherein the replication competent AAV virus is a wild type serotype-2 AAV.

8. A method of producing an antiviral vector comprising:
culturing the antiviral vector with a population of cells infected with a first THV, such that the antiviral vector co-infects the population of cells; and
isolating the antiviral vector after at least one full infectious cycle;
wherein the antiviral vector comprises a replication competent AAV virus and a nucleotide sequence that encodes an RNAi molecule that inhibits expression of a targeted helper virus (THV) gene, and
wherein the RNAi molecule is an shRNA comprising a sequence selected from the group consisting of SEQ ID NO:4, SEQ ID NO:5, SEQ ID NO:6, SEQ ID NO:7, SEQ ID NO:8, SEQ ID NO:15, SEQ ID NO:16, SEQ ID NO:17, SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:57, SEQ ID NO:58, and SEQ ID NO:59.

9. The method of claim 8, wherein the THV gene is part of an Adenovirus (Ad) genome, a Human Papillomavirus (HPV) genome, a Human Herpes Virus (HHV) genome, or a Vaccinia virus (VV) genome.

10. The method of claim 9, wherein the THV gene is HPV E6 or HPV E7.

11. The method of claim 9, wherein the THV gene is Ad E1, Ad IVa, or Ad Hexon.

12. The method of claim 9, wherein the RNAi molecule targets Ad Tripartite Leader Sequence (TriP).

13. The pharmaceutical composition of claim 1, comprising two or more antiviral vectors, wherein the inhibitory expression cassettes of the antiviral vectors comprise nucleotide sequences that encode RNAi molecules that inhibit expression of different THV genes.

* * * * *